US012778978B2

(12) United States Patent
Crouzier et al.

(10) Patent No.: US 12,778,978 B2
(45) **Date of Patent: *Nov. 3, 2026**

(54) VAGINAL CONTRACEPTIVE COMPOSITION FOR REINFORCEMENT OF MUCUS BARRIER PROPERTIES

(71) Applicant: CIRQLE BIOMEDICAL CONTRACEPTION ApS, Copenhagen N (DK)

(72) Inventors: Thomas Crouzier, Sundbyberg (SE); Ulrike Schimpf, Stockholm (SE)

(73) Assignee: CIRQLE BIOMEDICAL CONTRACEPTION APS, Copenhagen N (DK)

( * ) Notice: Subject to any disclaimer, the term of this patent is extended or adjusted under 35 U.S.C. 154(b) by 671 days.

This patent is subject to a terminal disclaimer.

(21) Appl. No.: 17/766,206

(22) PCT Filed: Oct. 9, 2020

(86) PCT No.: PCT/DK2020/050282
§ 371 (c)(1),
(2) Date: Apr. 1, 2022

(87) PCT Pub. No.: WO2021/069046
PCT Pub. Date: Apr. 15, 2021

(65) Prior Publication Data

US 2024/0082293 A1 Mar. 14, 2024

(30) Foreign Application Priority Data

Oct. 11, 2019 (EP) .................................... 19202690

(51) Int. Cl.

| | |
|---|---|
| ***A61K 9/00*** | (2006.01) |
| ***A61K 31/722*** | (2006.01) |
| ***A61K 31/785*** | (2006.01) |
| ***A61K 47/38*** | (2006.01) |
| ***A61P 15/18*** | (2006.01) |

(52) U.S. Cl.
CPC .......... *A61K 31/722* (2013.01); *A61K 9/0034* (2013.01); *A61K 31/785* (2013.01); *A61K 47/38* (2013.01); *A61P 15/18* (2018.01)

(58) Field of Classification Search
None
See application file for complete search history.

(56) References Cited

U.S. PATENT DOCUMENTS

| | | | |
|---|---|---|---|
| 4,474,769 A | 10/1984 | Smith | |
| 2006/0018951 A1* | 1/2006 | Maniar | A61K 9/7007 424/443 |
| 2017/0224749 A1* | 8/2017 | Palmeira De Oliveira | A61K 31/7056 |
| 2024/0082293 A1 | 3/2024 | Crouzier et al. | |

FOREIGN PATENT DOCUMENTS

| | | | | |
|---|---|---|---|---|
| CN | 102895256 A | 1/2013 | | |
| CN | 108158995 A | 6/2018 | | |
| EP | 3804695 A1 | 4/2021 | | |
| RU | 2494746 C1 | 10/2013 | | |
| WO | WO 00/15192 A1 | 3/2000 | | |
| WO | WO 01/66084 A2 | 9/2001 | | |
| WO | WO 2005/013906 A2 | 2/2005 | | |
| WO | WO 2005/013906 A3 | 7/2006 | | |
| WO | WO-2018185321 A1 * | 10/2018 | | A61K 31/717 |

OTHER PUBLICATIONS

Acarturk, "Mucoadhesive Vaginal Drug Delivery Systems", Recent Patents on Drug Delivery & Formulation, 2009, 3: 193-205.
Carneiro et al., "BSA and Fibrinogen Adsorption on Chitosan/k-Carrageenan Polyelectrolyte Complexes", Macromolecular Bioscience, 2013, 13: 1072-1083.
Chemicalbook entry for Lactic Acid, CAS 50-21-5, downloaded from www.chemicalbook.com, 2026.
Denuziere et al., "Chitosan-chondroitin sulfate and chitosan-hyaluronate polyelectrolyte complexes: biological properties", Biomaterials, 1998, 19: 1275-1285.
Kawarkhe et al., "Designing of the Mucoadhesive Intravaginal Spermicidal Films", Indian Journal of Pharmaceutical Sciences, 2010, 72(5): 652-655.
Li et al., "Drug-free and non-crosslinked chitosan scaffolds with efficient antibacterial activity against both Gram-negative and Gram-positive bacteria", Carbohydrate Polymers, May 11, 2020, 241: 116386.
Luppi et al., "Novel mucoadhesive nasal inserts based on chitosan/hyaluronate polyelectrolyte complexes for peptide and protein delivery", Journal of Pharmacy and Pharmacology, 2009, 61: 151-157.
(Continued)

*Primary Examiner* — Brian Gulledge
(74) *Attorney, Agent, or Firm* — James S. Keddie; Bozicevic, Field & Francis LLP

(57) ABSTRACT

The disclosure relates to a vaginal contraceptive composition comprising one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group. The disclosure further relates to a use of a vaginal contraceptive composition, a vaginal contraceptive composition for use in therapy, a vaginal contraceptive composition for use as a contraceptive or contraceptive agent and a vaginal contraceptive composition for use in birth control or birth control therapy.

20 Claims, 31 Drawing Sheets

(56) References Cited

OTHER PUBLICATIONS

Maslarska et al., "HPLC Method for Simultaneous Determination of Metronidazole and Preservatives in Vaginal Gel Formulation", Acta Chromatographica, May 9, 2017, 30(2): 127-130.
Takayama et al., "Effect of Interpolymer Complex Formation on Bioadhesive Property and Drug Release Phenomenon of Compressed Tablet Consisting of Chitosan and Sodium Hyaluronate", Chem. Pharm. Bull. 1990, 38 (7): 1993-1997.
Wang et al., "Precise quantification of the antibacterial activity of chitosan by NB medium neutralizer", Journal of Materials Science & Technology, Sep. 11, 2020, 70: 224-232.
Wang et al., "Quantitative evaluation of the antibacterial effectiveness and efficiency of chitosan considering the effect of neutralization", Carbohydrate Polymers, Mar. 5, 2021, 265: 117918.

* cited by examiner

VAGINAL CONTRACEPTIVE COMPOSITION FOR REINFORCEMENT OF MUCUS BARRIER PROPERTIES

CROSS-REFERENCE TO RELATED APPLICATIONS

This application is a § 371 national phase of International Application No. PCT/DK2020/050282, filed on Oct. 9, 2020, which claims the benefit of European Application No. 19202690.4, filed on Oct. 11, 2019, which application is incorporated by reference herein.

TECHNICAL FIELD

The invention relates to a vaginal contraceptive composition comprising one or more active ingredients and a physiological acceptable gelling agent, wherein at least one of the one or more active ingredients is a mucoadhesive polymer. The invention also relates to uses of such a vaginal contraceptive composition in therapy or contraception. The mucoadhesive polymer can cross-link the mucus layer without aggregating the mucus.

BACKGROUND ART

The citation and incorporation of patent documents herein is done for convenience only and does not reflect any view of the validity, patentability, and/or enforceability of such patent documents.

There is a rapidly growing number of women that are unhappy with hormonal contraceptives but cannot find alternatives that are both convenient (no implantations, easy to use, flexible to use) and effective (over 90% efficacy in a typical use case). Indeed, 125 million couples in Europe and the US use birth control and hormonal contraceptives (pill, patch, implant, ring, etc.) are by far the most used birth control method. However, an increasing awareness of the side effects caused by hormones is upending the market for contraceptives. There are now robust evidence for side effects of hormonal contraceptives. Three studies including between 0.5 million and 1.8 million women show that the use of hormonal contraceptives increases women's rate of taking antidepressants by 23% and for teens the rate nearly doubles (Charlotte Wessel Skovlund, Lina Steinrud Morch, Lars Vedel Kessing, and Øjvind Lidegaard. 2016. "Association of Hormonal Contraception With Depression." JAMA Psychiatry 73 (11): 1154-62), increases women's rate of suicide attempt by 197% and the suicide rate by 308% (Charlotte Wessel Skovlund, Lina Steinrud Morch, Lars Vedel Kessing, Theis Lange, and Øjvind Lidegaard. 2017. "Association of Hormonal Contraception With Suicide Attempts and Suicides." The American Journal of Psychiatry, November) and increases the risk of developing breast cancer by 9% when used for less than a year and up to 38% when used for 10 years (Lina S. Morch, Charlotte W. Skovlund, Philip C. Hannaford, Lisa Iversen, Shona Fielding, and Øjvind Lidegaard. 2017. "Contemporary Hormonal Contraception and the Risk of Breast Cancer." The New England Journal of Medicine 377 (23): 2228-39). Many women now wish to move away from hormonal contraception, but they are unable to find suitable alternatives. The current alternatives are either inconvenient (condoms, diaphragms) or invasive (copper and hormone eluting implants) and can be poorly effective in actual use case (for instance condoms are only 85% effective on average).

There are over 400 square meters of epithelial surfaces hidden within the body of a human being, including the lung, gastrointestinal tract, and the female reproductive tract. The wet epithelial surfaces rely on a mucus gel for protection from dehydration, shear stress, and infections. Besides water, mucus mainly contains mucin biopolymers mixed with proteins, lipids, and salts.

Mucins are large glycoproteins, which consist of an extended central protein core densely conjugated with oligosaccharides that can account for up to 50% of the molecule's molecular weight. Mucins have a central role in the protective function, creating a barrier, which serves as a size exclusion and affinity-based selective filter, preventing many deleterious molecules from reaching the epithelial surface.

Mucoadhesive polymers have been used for drug delivery due to their adhesive properties. For instance, they have been used to deliver drugs to inflammation sites.

Mucoadhesive polymers are typically assembled into materials or a gel alongside a drug, the intent being to concentrate the drug at the surface of the mucus layer and improve drug delivery.

WO2004069230 relates to pharmaceutical compositions containing a physiologically active agent, i.e. a drug, and a release sustaining or mucoadhesive agent e.g. chitosan, which serves to prolong the release of the active agent from the composition.

Another use for chitosan is in female contraception. One example of such may be found in CN102895256, which relates to chitosan gel foaming agent suitable for a female contraception and fungicidal effect and a preparation method thereof, and belongs to the technical field of foaming agent production. According to this disclosure, chitosan molecules are trapped in a solid foam matrix in association with polyacrylic acid, which physically prevents sperm passage. Additionally, the chitosan has a molecular weight distribution of 2000-5000 Da, a deacetylation degree above 95%, and a concentration of 5-10 wt. %, whereas the polyacrylic acid is in a concentration of 1-3 wt. %.

Another example of chitosan for female contraception may be found in WO2018185321, which relates to a mucoadhesive polymer, more specifically chitosan, which can cross-link the mucus layer without aggregating the mucus. The chitosan consisting of 4 to 20 monomer units and a deacetylation degree above 50%.

A third example may be found in U.S. Pat. No. 4,474,769, which relates to a method for injecting chitosan formulation directly in the uterine cavity of the female for a prolonged period to kill or inactivate mammalian spermatozoa.

It is known that mucoadhesive molecules promote the tightness and thickening of the mucosal tissue or enhance the barrier function, but usage has shown that the mucoadhesive polymers and the mucus-penetrating nanoparticles will cross-link and aggregate the mucus, leading to the formation of a highly swollen interpenetrating polymeric network. Aggregation of the mucus thus results in opening of pores within the mucus and causes a weakening of the barrier properties of the mucus. There is therefore still a need within the field for a composition, which shows improvement of cross-linking the mucus without aggregation.

Hence, it is an object of the invention to provide a mucoadhesive polymer, which can cross-link the mucus layer of the female cervical entrance, i.e. the exocervix, without aggregating the mucus, or with a lesser extent of aggregation compared to previous compositions in the art. The exocervix is the protective mucous membrane on the exterior of the cervix. Preferably, the mucoadhesive polymer may also cross-link the mucus layer of the female cervical entrance at the endocervix, which is the mucous membrane of the cervical canal. The cross-linking should be such that it is sufficient to prevent motile sperm from movement through the mucus layer.

Another object of the invention is to provide a mucoadhesive polymer, which provides a more reliable barrier effect for preventing cells and microorganisms such as bacteria, viruses, and/or spermatozoa to penetrate the cross-linked mucus and diffuse into the mucosa membrane.

Yet another object of the invention is to provide a mucoadhesive polymer, which provides a sufficient barrier effect for preventing pregnancy and/or sexually transmitted infections (STI).

SUMMARY

In here is disclosed a newly developed technology that offers an alternative to hormonal contraception that is non-invasive convenient to use and effective. The strategy relies on making cervical mucus, the body's natural barrier between the vagina and the uterus, temporarily impenetrable for sperm cells. Cervical mucus protects women from infections and is mostly impenetrable to foreign cells throughout the month. However, around the day of ovulation, hormonal changes trigger a loosening of the mucus, which then becomes highly penetrable to sperm cells. It was found that the delivery of mucoadhesive (bio) polymers to the cervical mucus could alter the microstructure of the mucus gel and hereby reinforce the body's own natural barrier and prevent fertilization.

It has previously been stipulated that a low molecular weight mucoadhesive polymer (see e.g. WO2018185321 or Biomacromolecules, 2018, 19, 3, 872-882) containing between 4 and 20 monomers was an ideal mucoadhesive polymer to reinforce the mucus barrier properties by cross-linking said mucus. It was the opinion that the small size of the polymer advantageously allowed the molecule to diffuse inside the mucus. This should improve diffusion of the mucoadhesive polymer into the mucus membrane allowing it to cross-link the mucus layer over a large thickness, without aggregating the mucus. The small mucoadhesive polymers complex would thereby block the pores of the network and reinforce the barrier properties. However, such reinforcement of the barrier properties by e.g. chitosan was shown to work for small chitosan size in pig gastric mucins and colonic mucin cell lines, but for application as a contraceptive composition, the mucus that needs to be targeted is very different from the mucin in the gastrointestinal tracts. At ovulation, the cervical mucus is loose as to allow sperm passage through the gel. Compared to gastric or colonic mucus, the mucin content is decreased and the general mucus structure and composition is very different. It is therefore very important that the mucus layer is cross-linked enough to sufficiently prevent motile sperm from movement through the mucus layer but without aggregating the mucus.

Aggregation of the mucus is occurring when the mucin polymers condense around the mucoadhesive polymers. The result of this is the creation of areas of very dense mucin polymer aggregates and the creation of areas of very open and very loose mucin network. These open areas can allow sperm to go through.

Therefore, the present invention relates to a vaginal contraceptive composition comprising one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Disclosed herein is shown that treatment with a 4 and 20 monomers mucoadhesive polymer as discussed above for gastric and colonic mucus is in fact not suitable for an effective reinforcement of the mucus barrier in the ovulatory mucus. Mucoadhesive polymers of at least 20.000 Da is shown to be much more effective at forming a barrier to e.g. sperm cells trying to penetrate the mucus barrier. Additionally, mucoadhesive polymers above 100.000 Da are herein shown to be too large and interact poorly with the mucus.

The composition as disclosed herein can efficiently be delivered to the cervix if formulated in a vaginal gel. The components of the gel could prevent diffusion of the mucoadhesive polymer from the gel into the mucus either by steric hindrance effects or by intermolecular interactions forming aggregates with the mucoadhesive polymer and gel, e.g. if the mucoadhesive polymer is provided as an excipient soft gel based on carboxymethyl cellulose (CMC), which is typically used as a gelling agent, this ingredient will strongly interact with e.g. chitosan, if used as the mucoadhesive polymer. At least two different types of gelling agents are suitable for vaginal formulation, natural and positively charged, without preventing penetration of the mucoadhesive polymer in the female ovulatory cervical mucus and without compromising the barrier reinforcement effect obtained by the mucoadhesive polymer. The gelling agents need to be either neutral or positively charged to avoid strong interactions with the mucoadhesive polymer. Another example is, that is that if the mucoadhesive polymer interacts with the mucus via thiol groups, then the excipients should not contain thiol groups.

The present invention further relates to the use of a vaginal contraceptive composition as a contraceptive agent, wherein said vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

The present invention also relates to a vaginal contraceptive composition for use in therapy, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Furthermore, the present invention relates to a vaginal contraceptive composition for use as a contraceptive or contraceptive agent, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

The present invention relates even further to a vaginal contraceptive composition for use in birth control or birth control therapy, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Lastly, the present invention relates to a method of therapy, a method of avoiding pregnancy, a method of contraception, and/or a method of birth control or birth control therapy, wherein the method(s) comprises the steps of using a vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

A, B, C—Left graphs are chitosan diffusion profiles in CVM for chitosan from crustacean shell origin of various molecular weight at an exposure time of 20 ms expressed in chitosan concentration (% w/v). Graphs on the right are diffusion profiles in CVM expressed as relative fluorescence intensities (RFI) of labelled chitosan from crustacean shell origin of various molecular weight measured by microscopy with an exposure time of 800 ms. The drop in fluorescence marks the maximum diffusion distance after 30 minutes of exposure to the mucus. All samples were dissolved in 32.5 mM LAC.

D, E, F, G, H—Left graphs are chitosan diffusion profiles in CVM for chitosan from non-animal origin of various molecular weight at an exposure time of 20 ms expressed in chitosan concentration (% w/v). Right graphs are chitosan diffusion profiles in CVM expressed as relative fluorescence intensities (RFI) of labelled chitosan from non-animal origin of various molecular weight measured by microscopy with an exposure time of 800 ms. The drop in fluorescence marks the maximum diffusion distance after 30 minutes of exposure to the mucus. Samples were dissolved in 32.5 mM LAC.

Figure 1A:
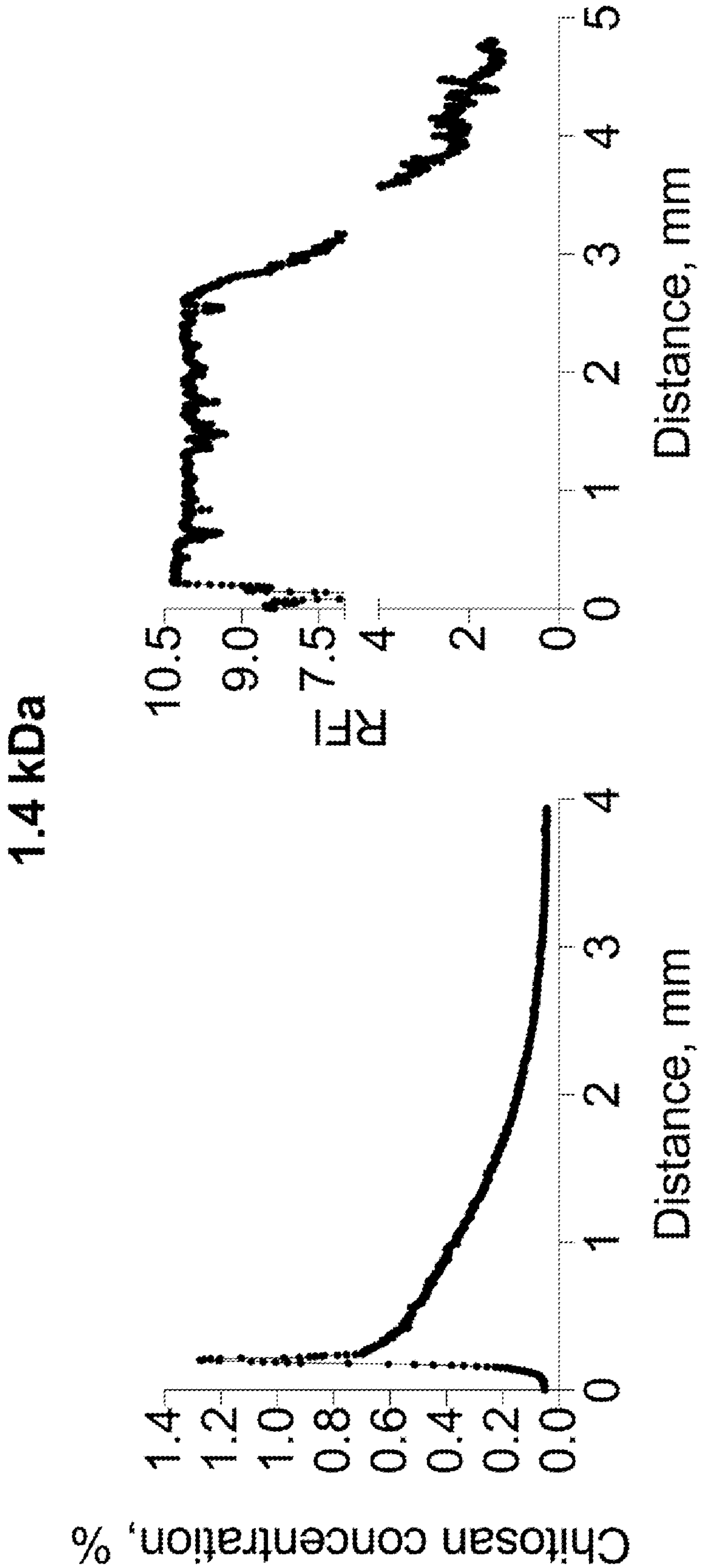
FIG. 1—Chitosan diffusion into cervical, ovulatory mucus: 0.5% CS/pH 5.5
Figure 1B:
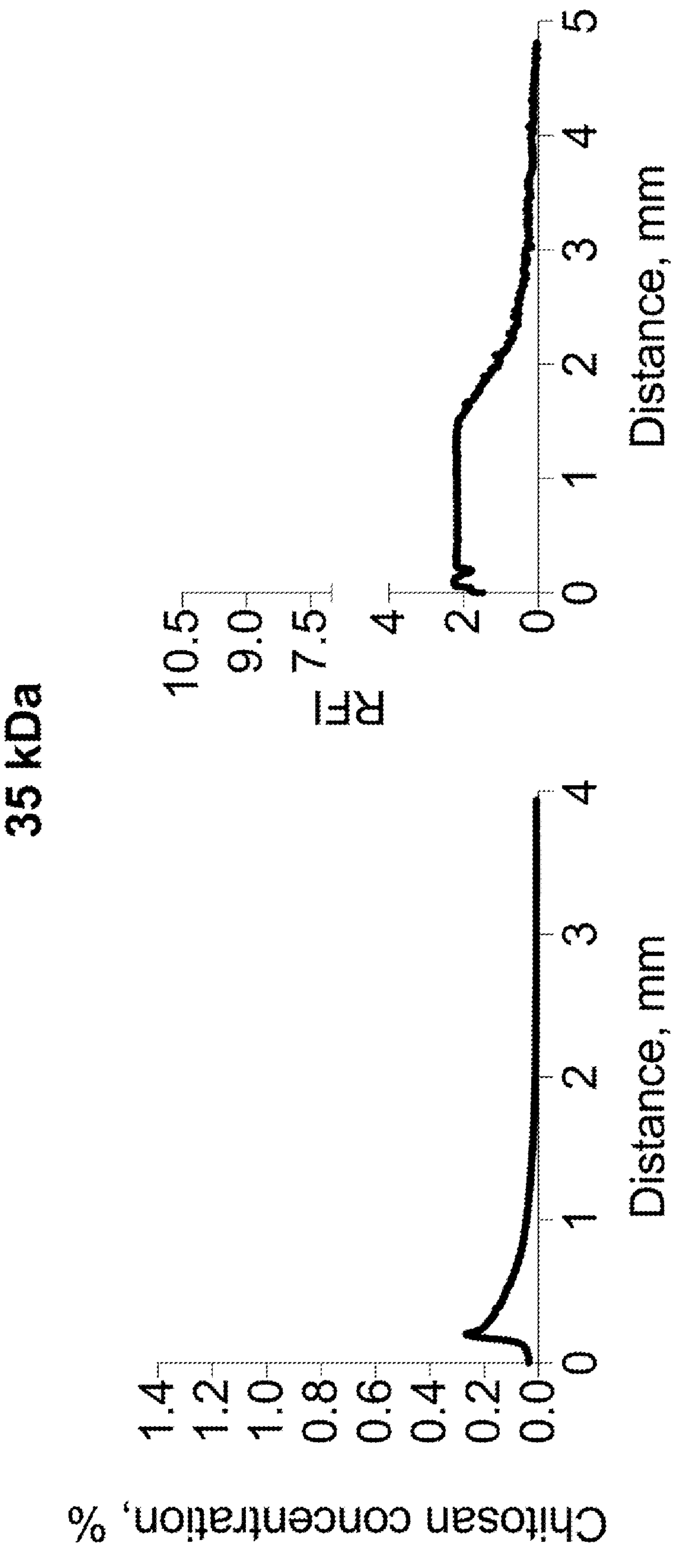
Figure 1C:
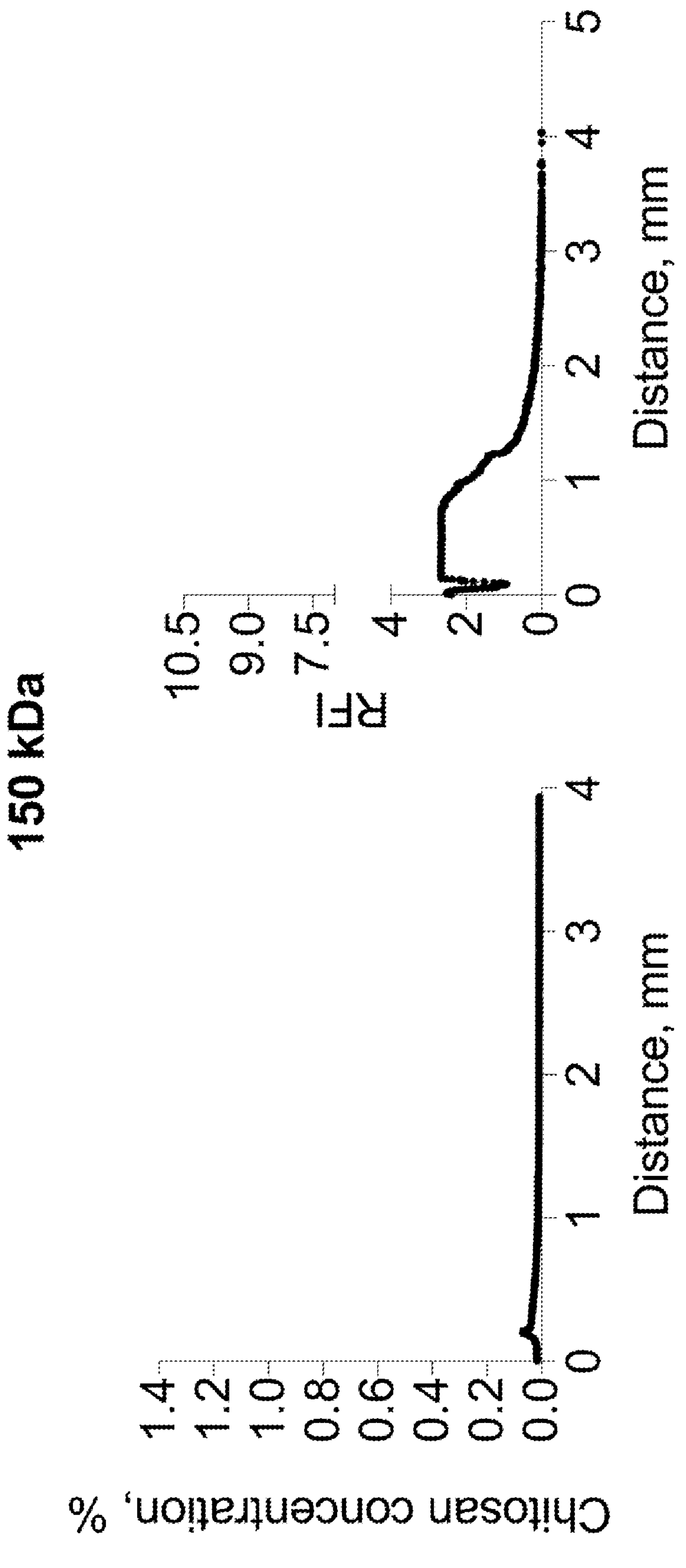
Figure 1D:
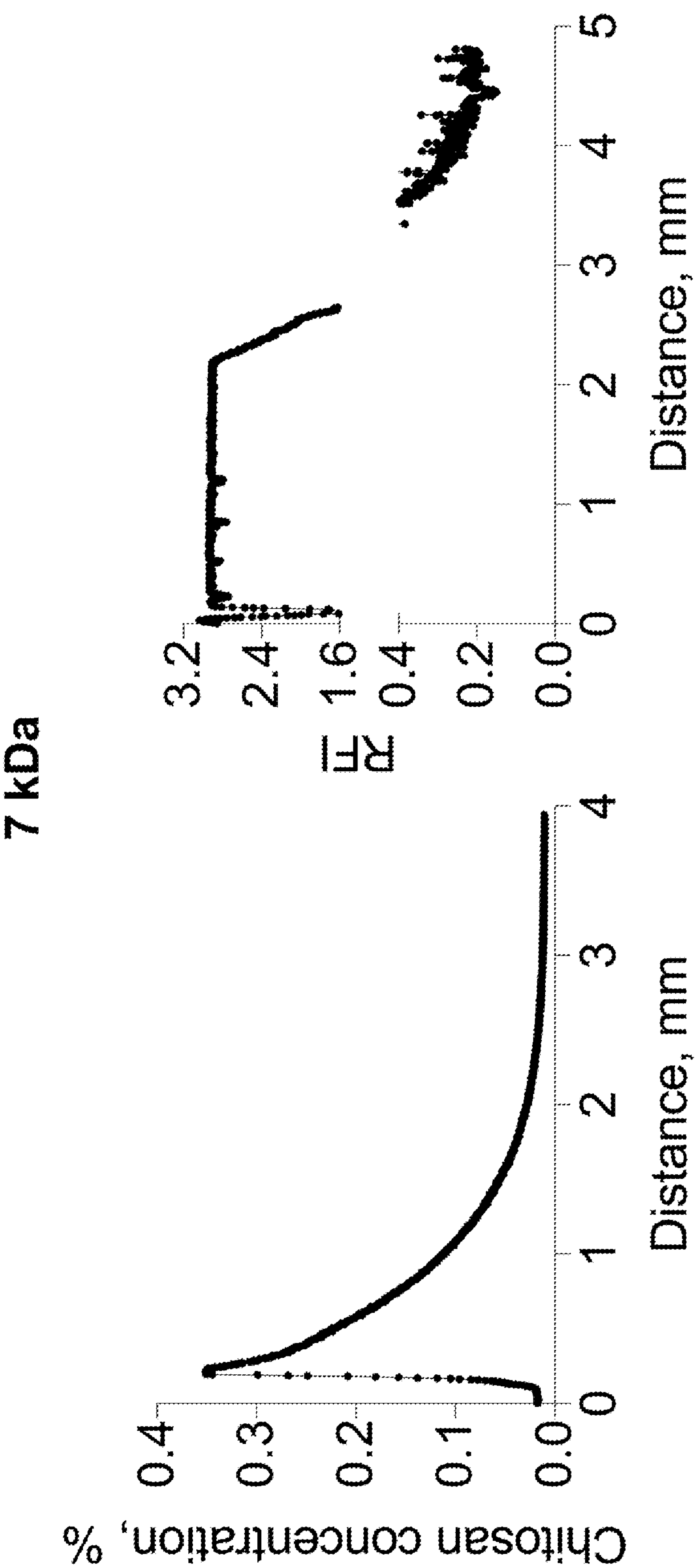
Figure 1E:
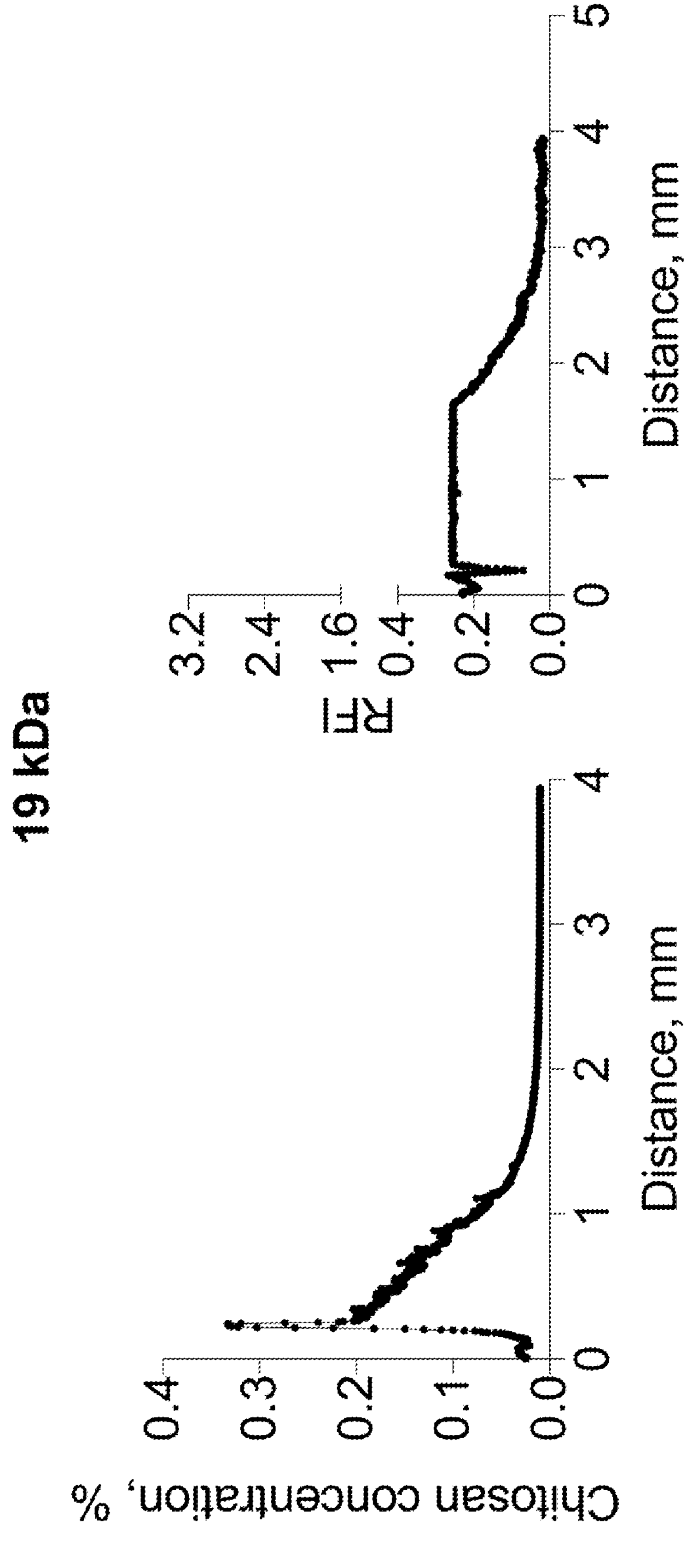
Figure 1F:
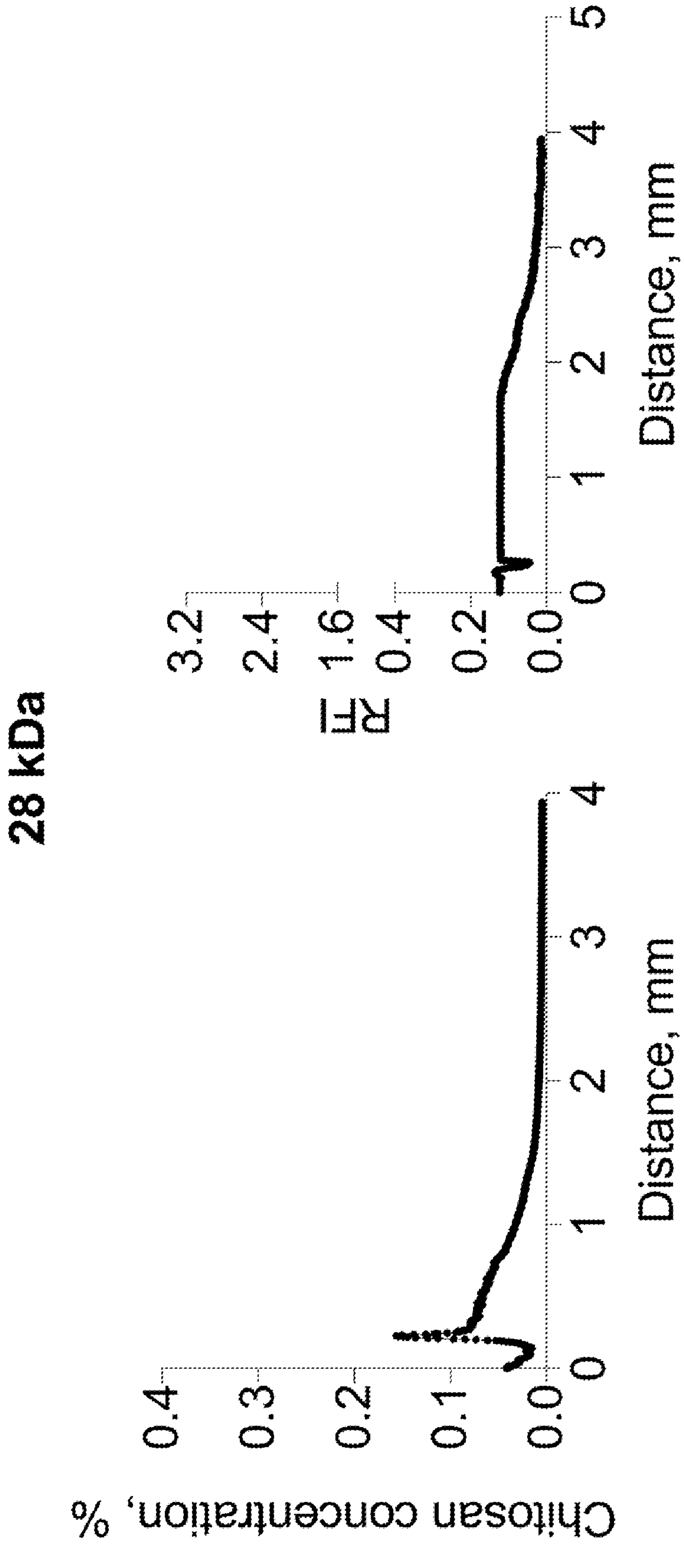
Figure 1G:
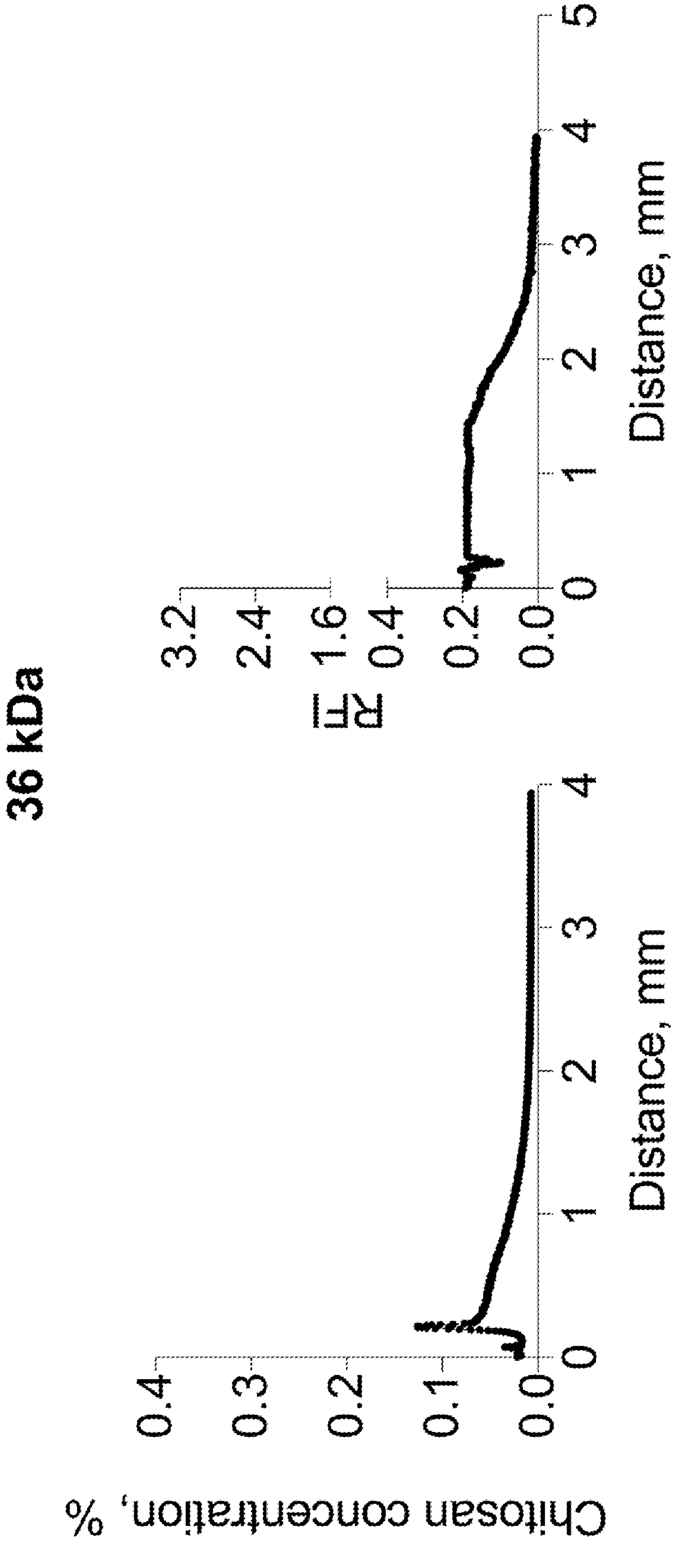
Figure 1H:
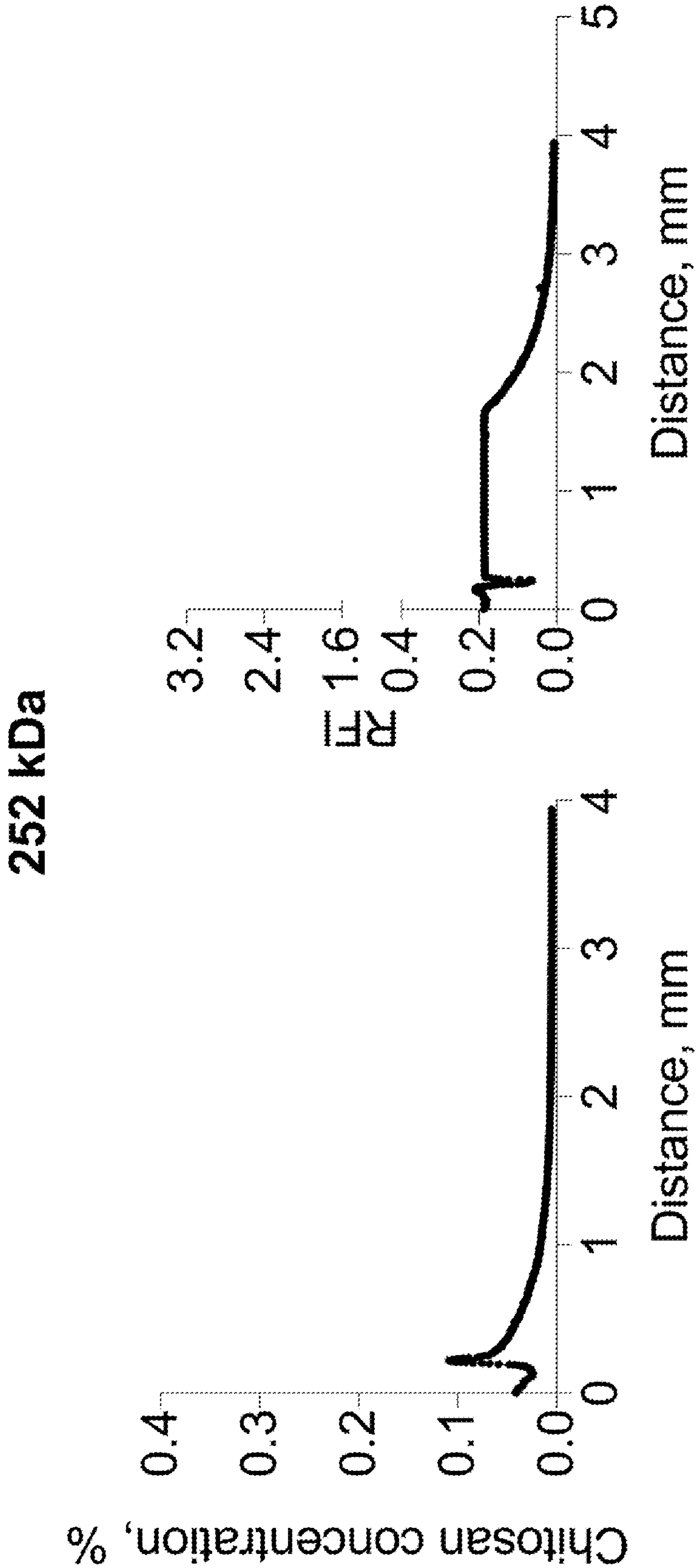
Figure 1I:
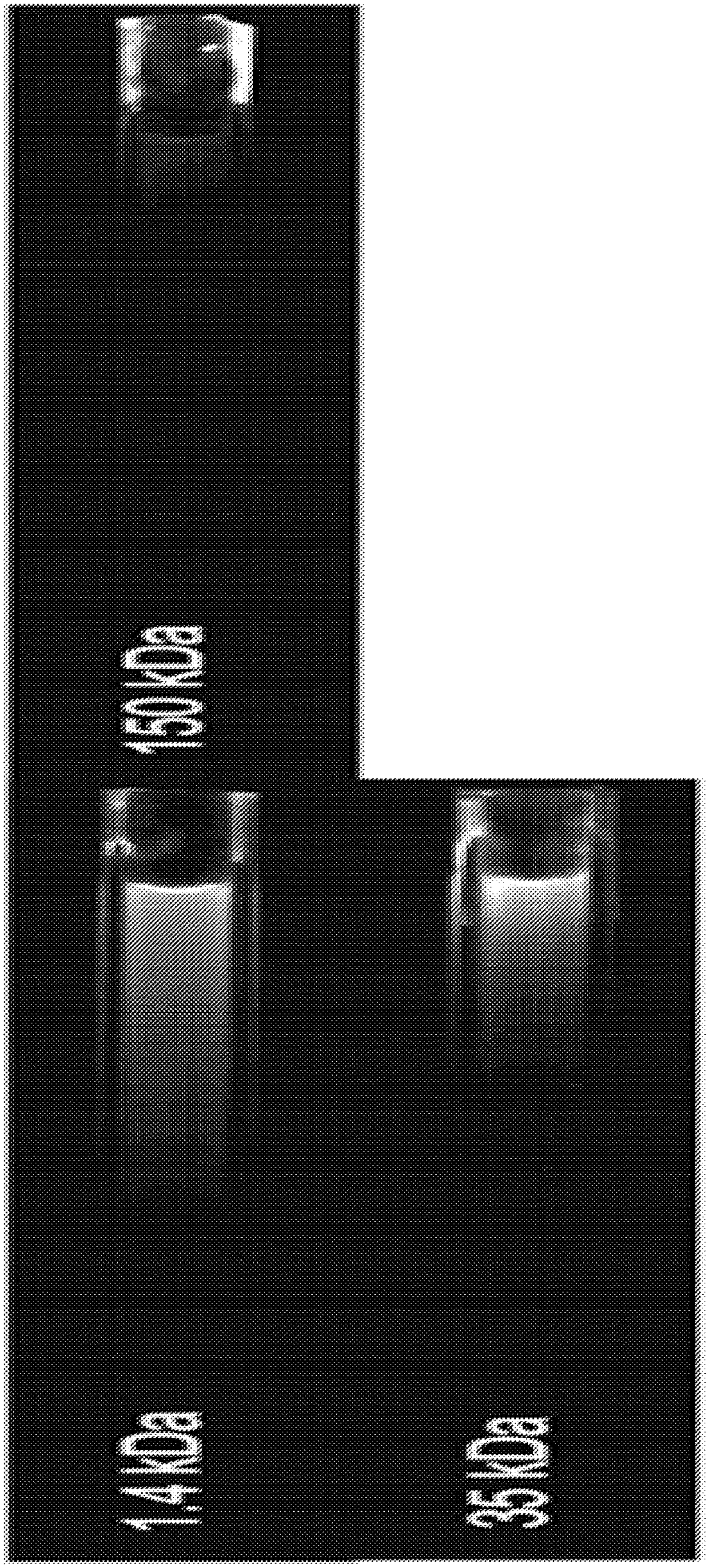

I—Representative images of the chitosans penetration tests performed with chitosans of various sizes. The intensity profiles were measured on these images to generate the graphs of FIG. 1A-C.

Figure 2:
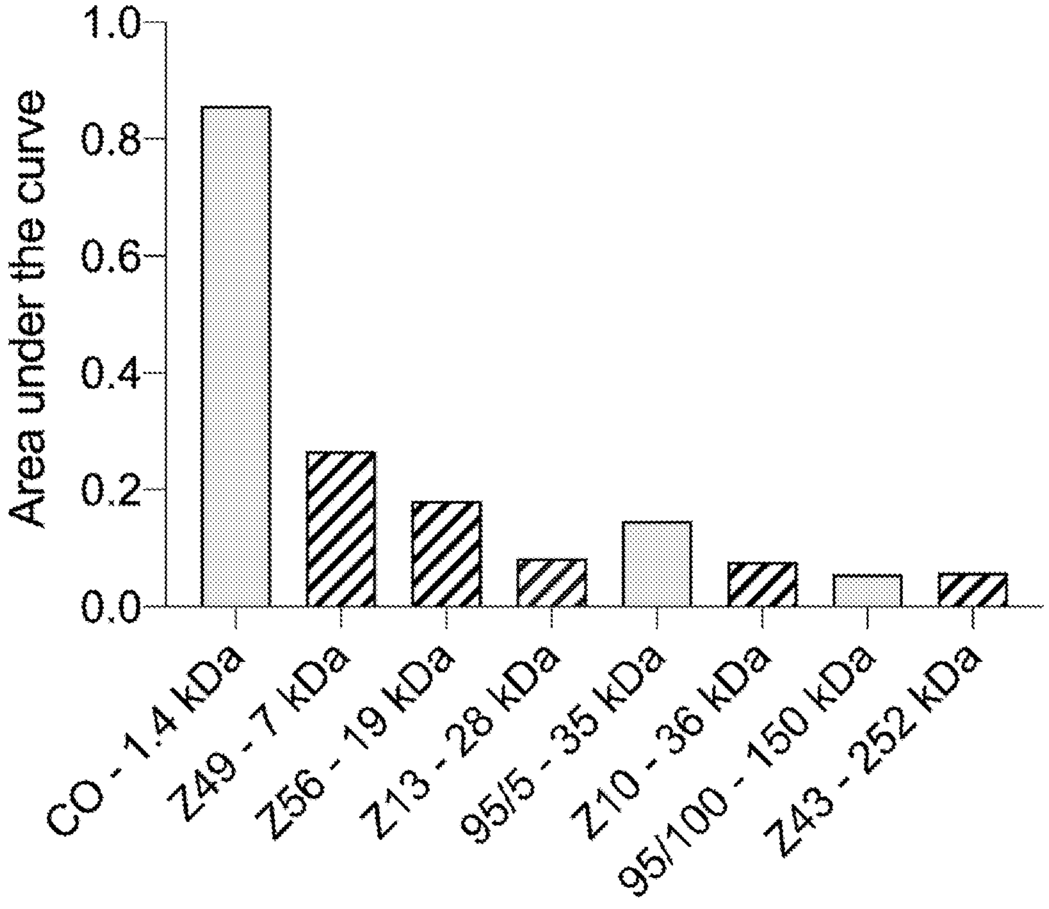

FIG. 2—Quantification of chitosan accumulation in human cervical ovulatory mucus after 30 minutes exposure as a function of chitosans molar mass.

Figure 3A:
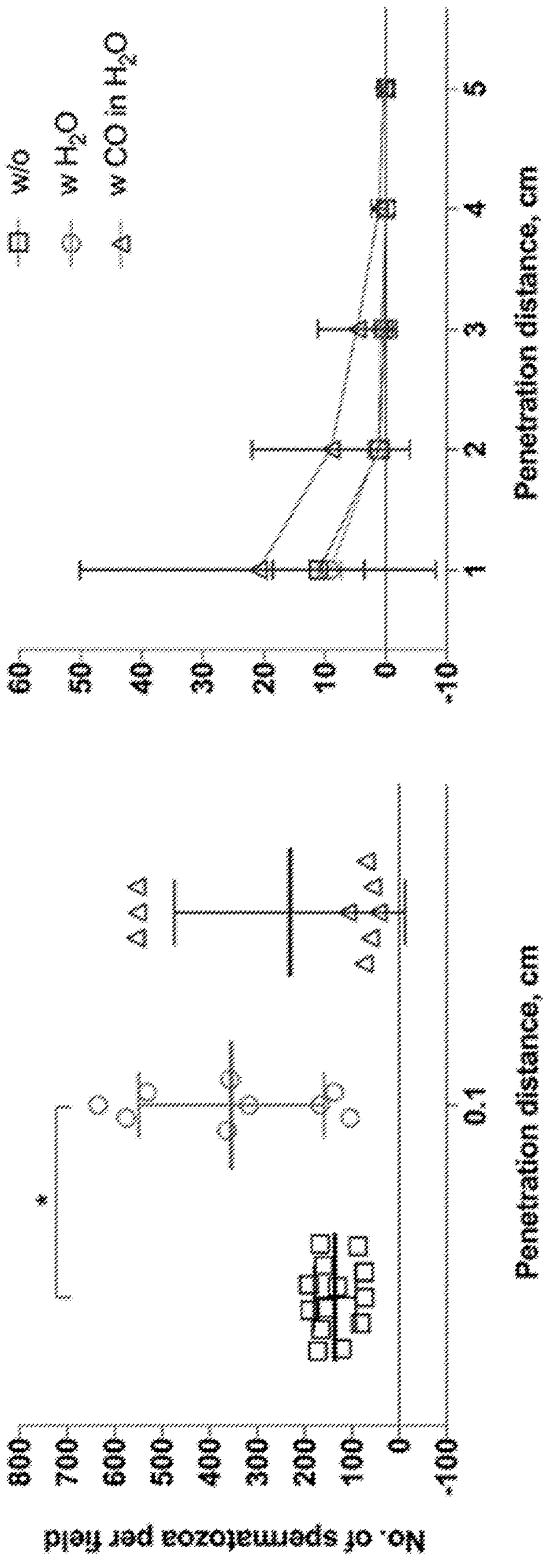
Figure 3B:
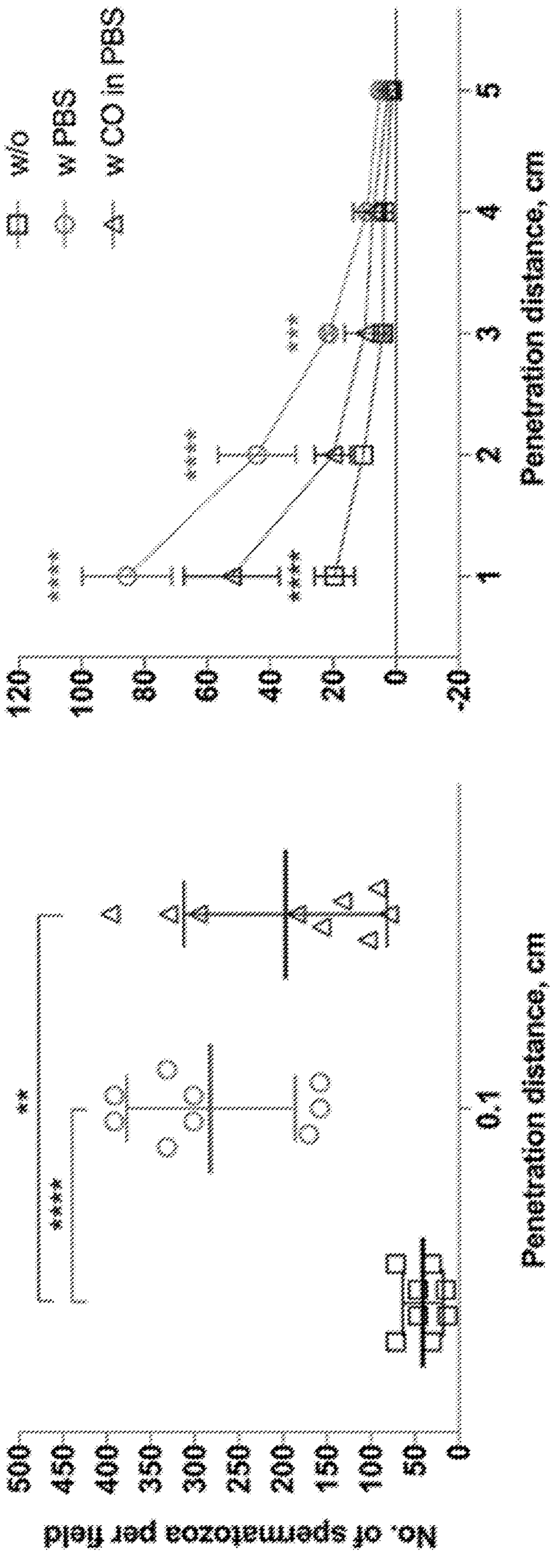
Figure 3C:
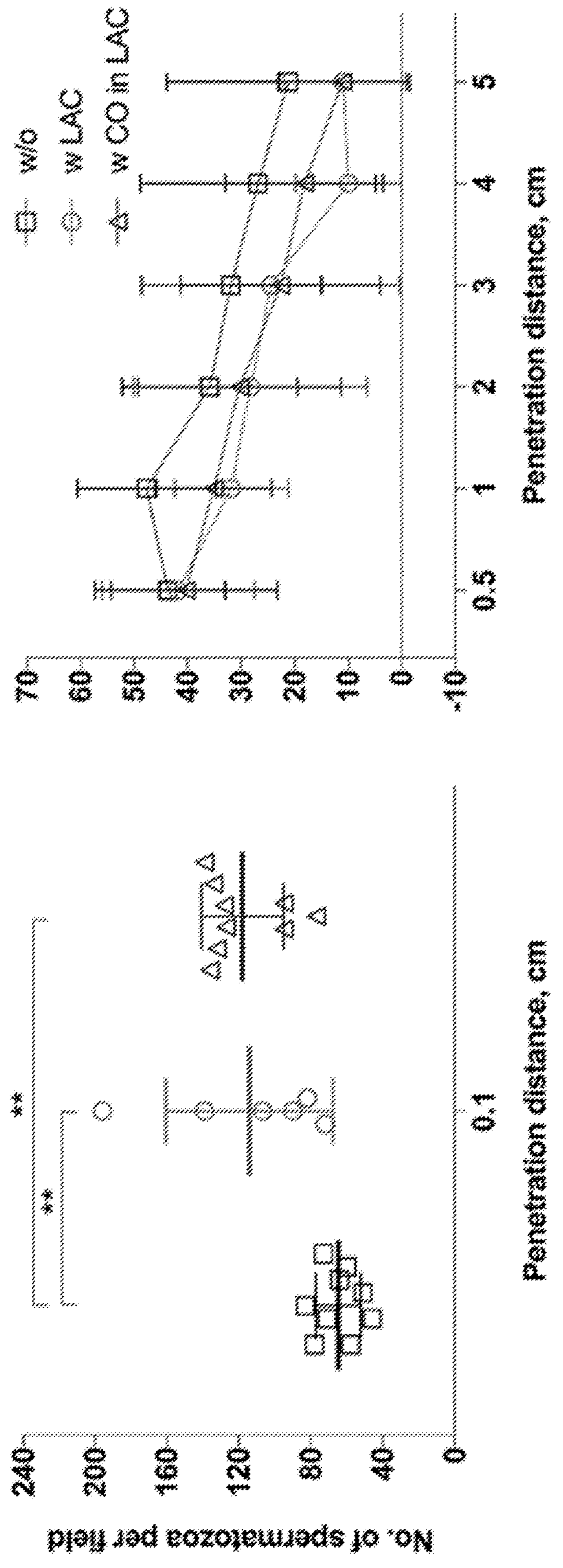
Figure 4A:
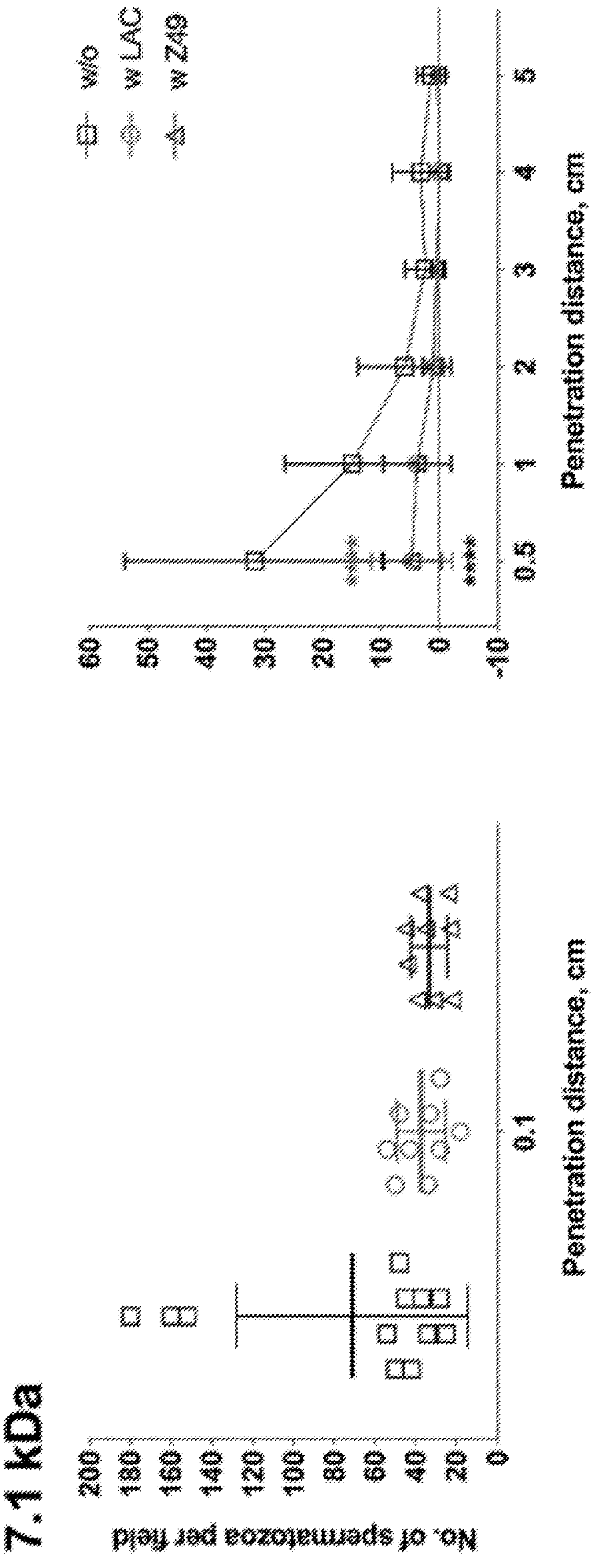
Figure 4B:
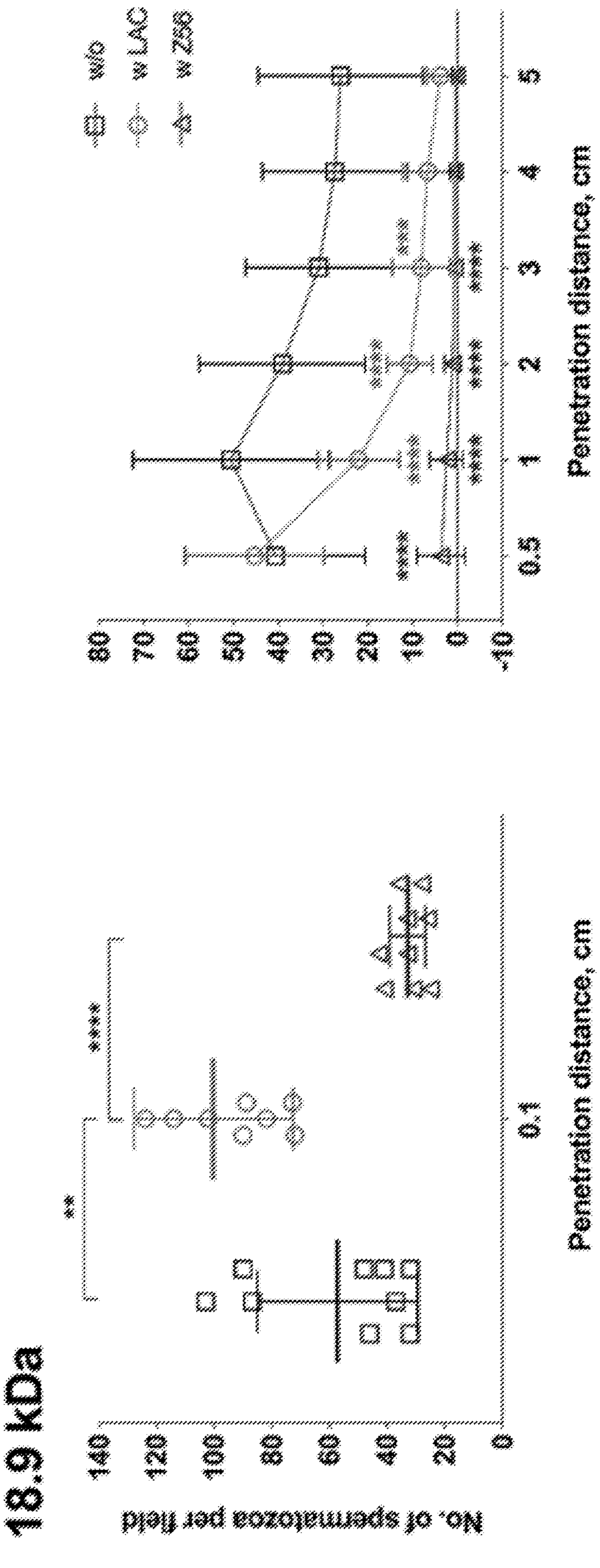
Figure 4C:
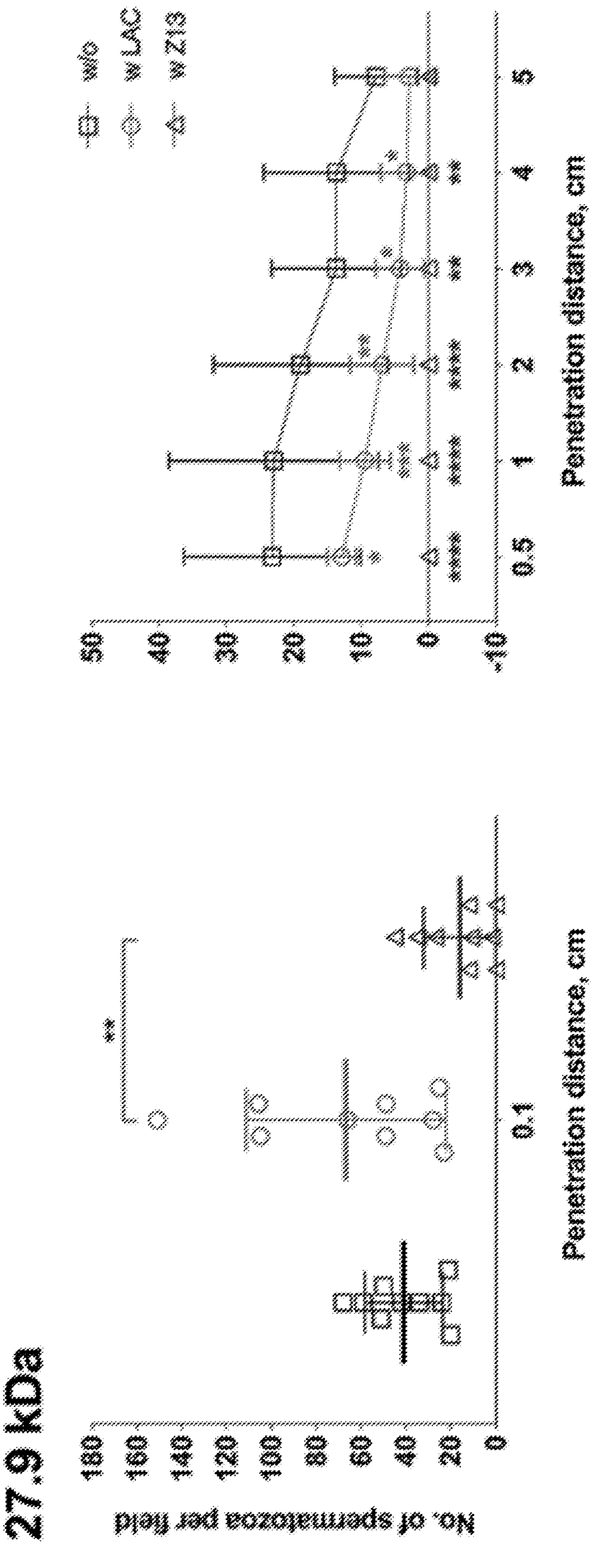
Figure 4D:
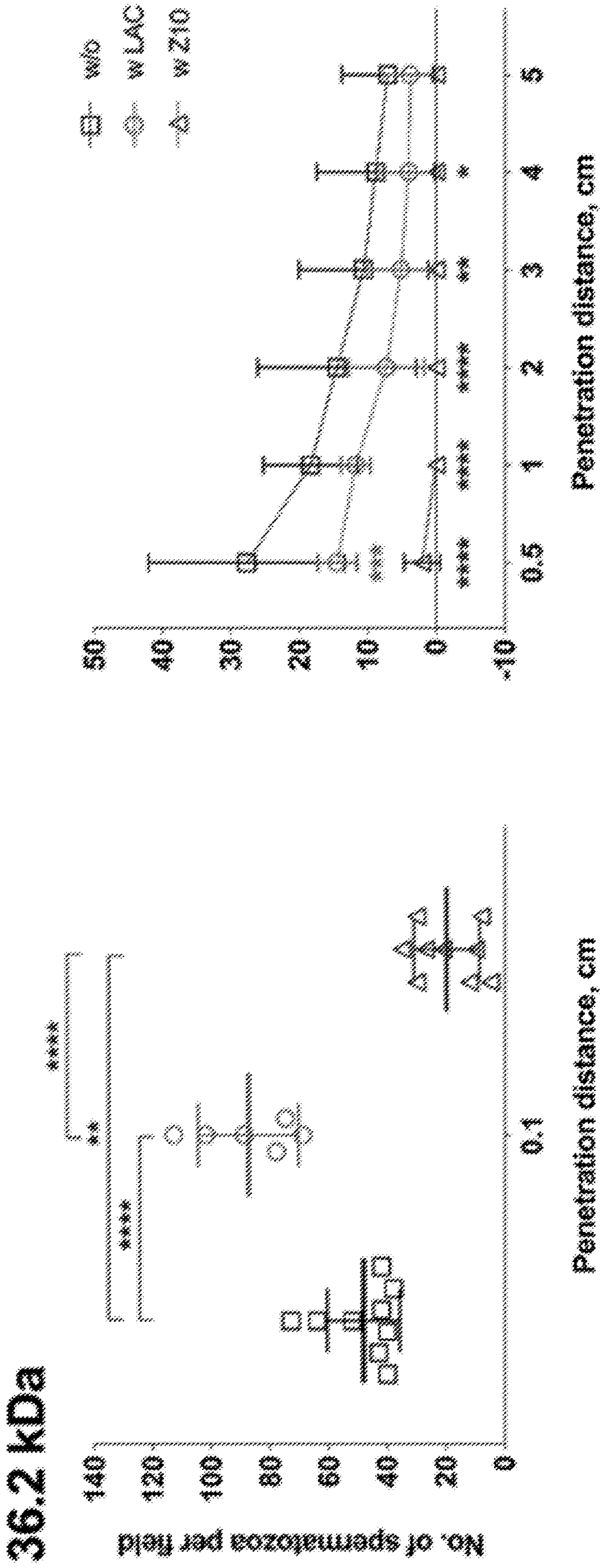
Figure 4E:
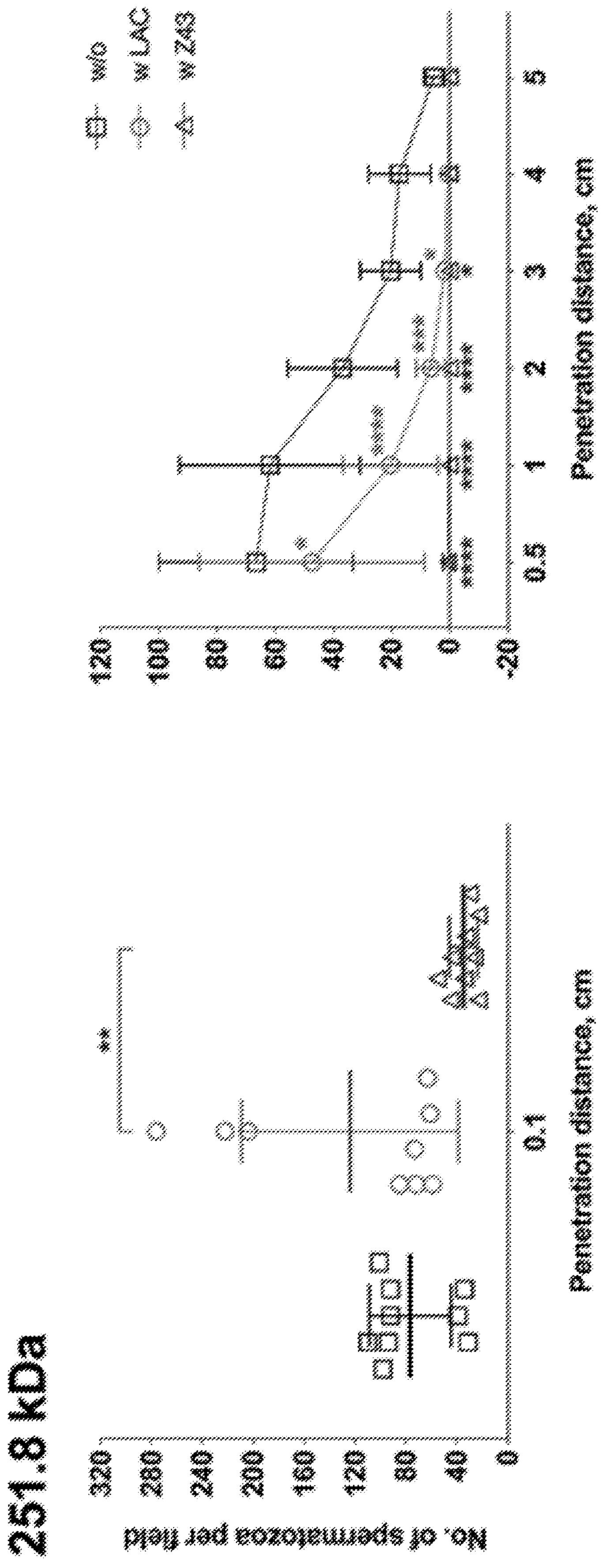
Figure 5A:
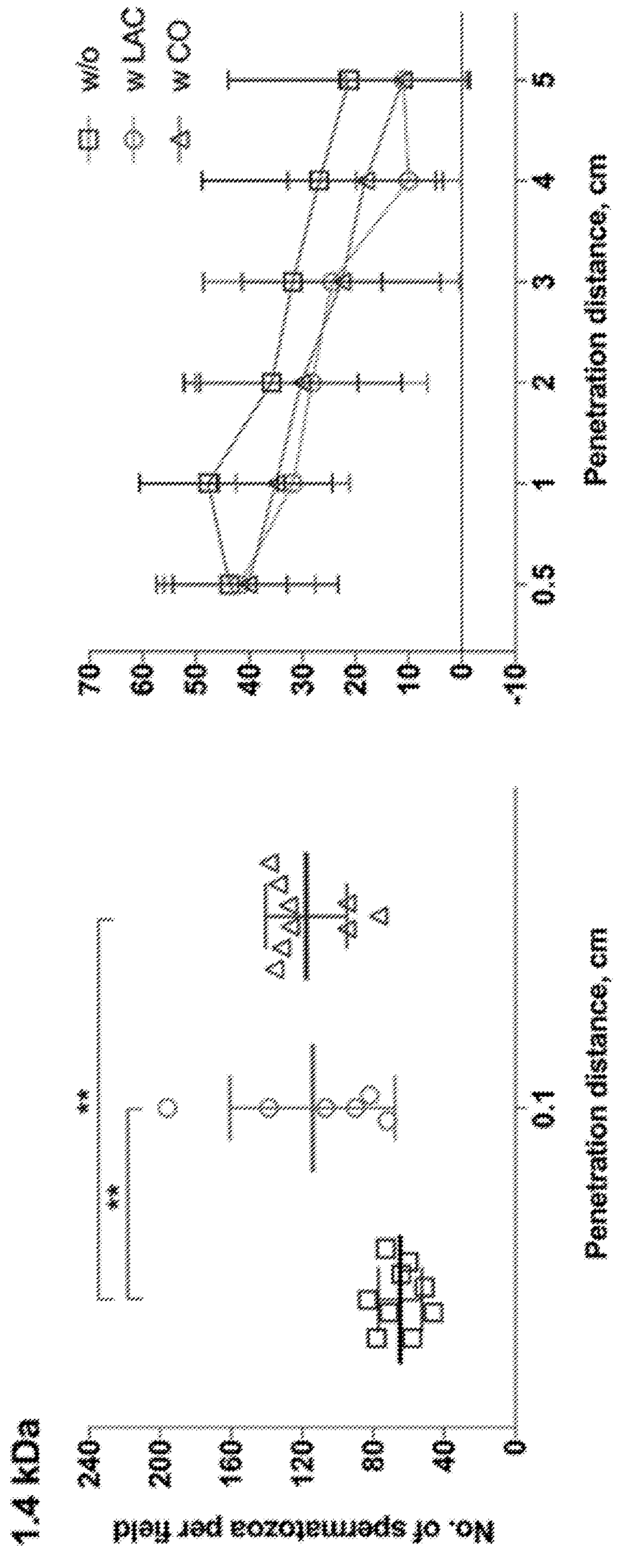
Figure 5B:
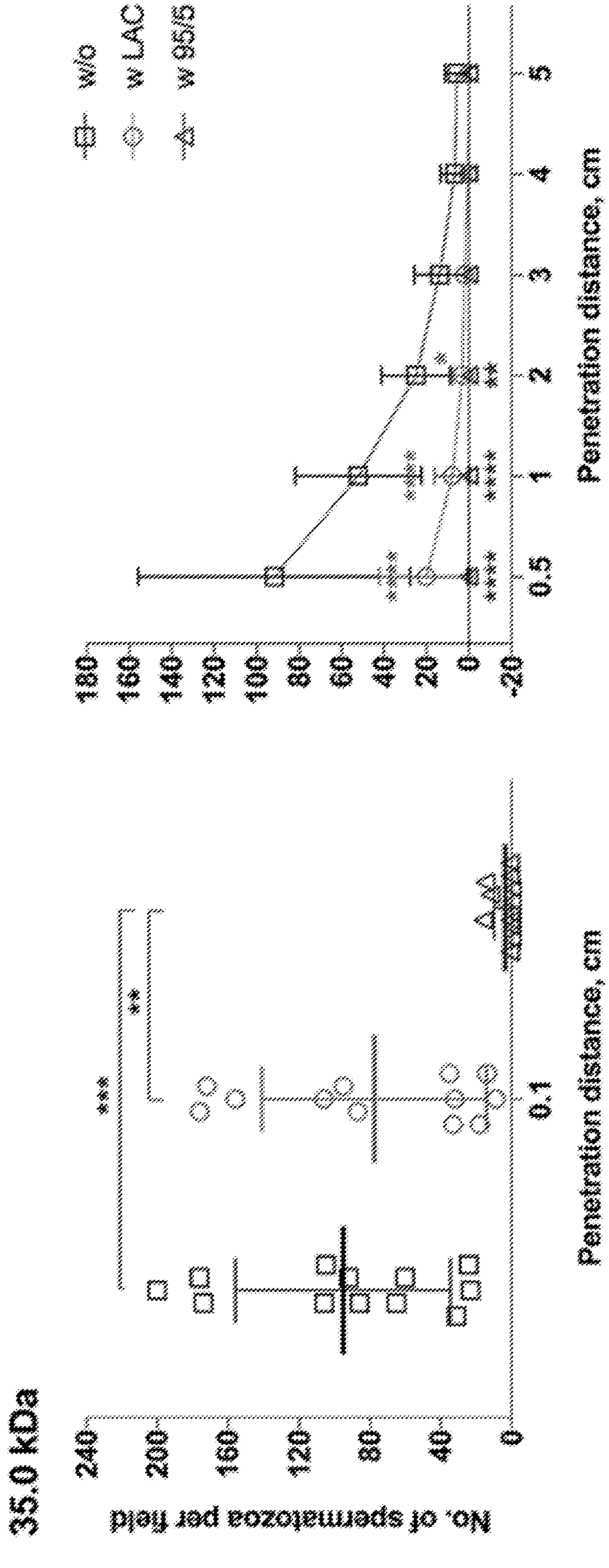
Figure 5C:
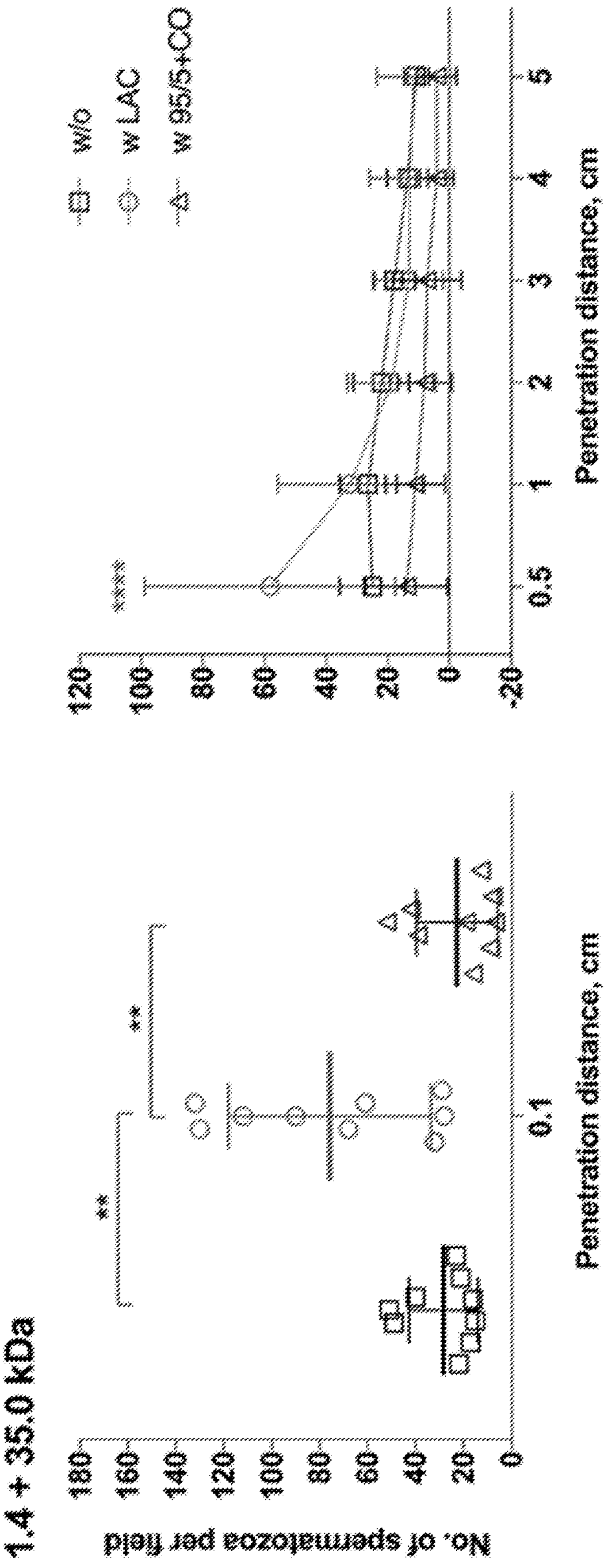
Figure 5D:
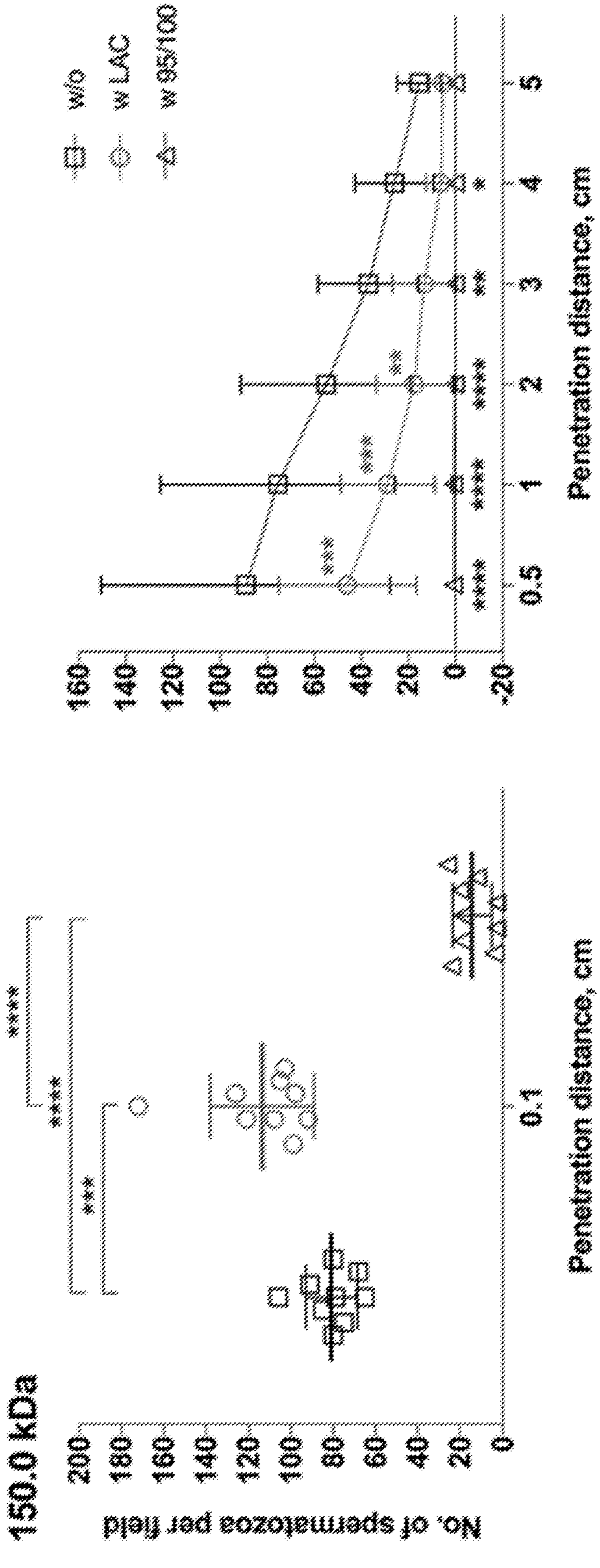

FIG. 3—Sperm penetration through cervical, ovulatory mucus: 0.5% (w/v) CO chitosan, in pH 5.5 solution containing only water ($H_2O$) (A), phosphate saline buffer (PBS) (B), or 100 mM lactic acid (LAC) (C).

FIG. 4—Sperm penetration through human cervical ovulatory mucus (A—7.1 kDa, B—18.9 kDa, C—27.9 kDa, D—36.2 kDa, and E—251.8 kDa). The mucus was either non-treated (w/o), treated with 32.5 mM lactic acid solution (LAC) (100 mM lactic acid solution for A—7.1 kDa), or treated with a fungal based chitosan dissolved in a 32.5 mM lactic acid solution (100 mM lactic acid solution for A—7.1 kDa). The molar mass of the chitosan used are indicated on the left-hand side of the graphs.

FIG. 5—Sperm penetration through human cervical ovulatory mucus (A—1.4 kDa, B—35.0 kDa, C—1.4 kDa+35.0 kDa, and D—150.0 kDa). The mucus was either non-treated (w/o), treated with 100 mM lactic acid solution (LAC), or treated with a crustacean shell based chitosan dissolved in a 100 mM lactic acid solution. The molar mass of the chitosan used are indicated on the left-hand side of the graphs.

Figure 6:
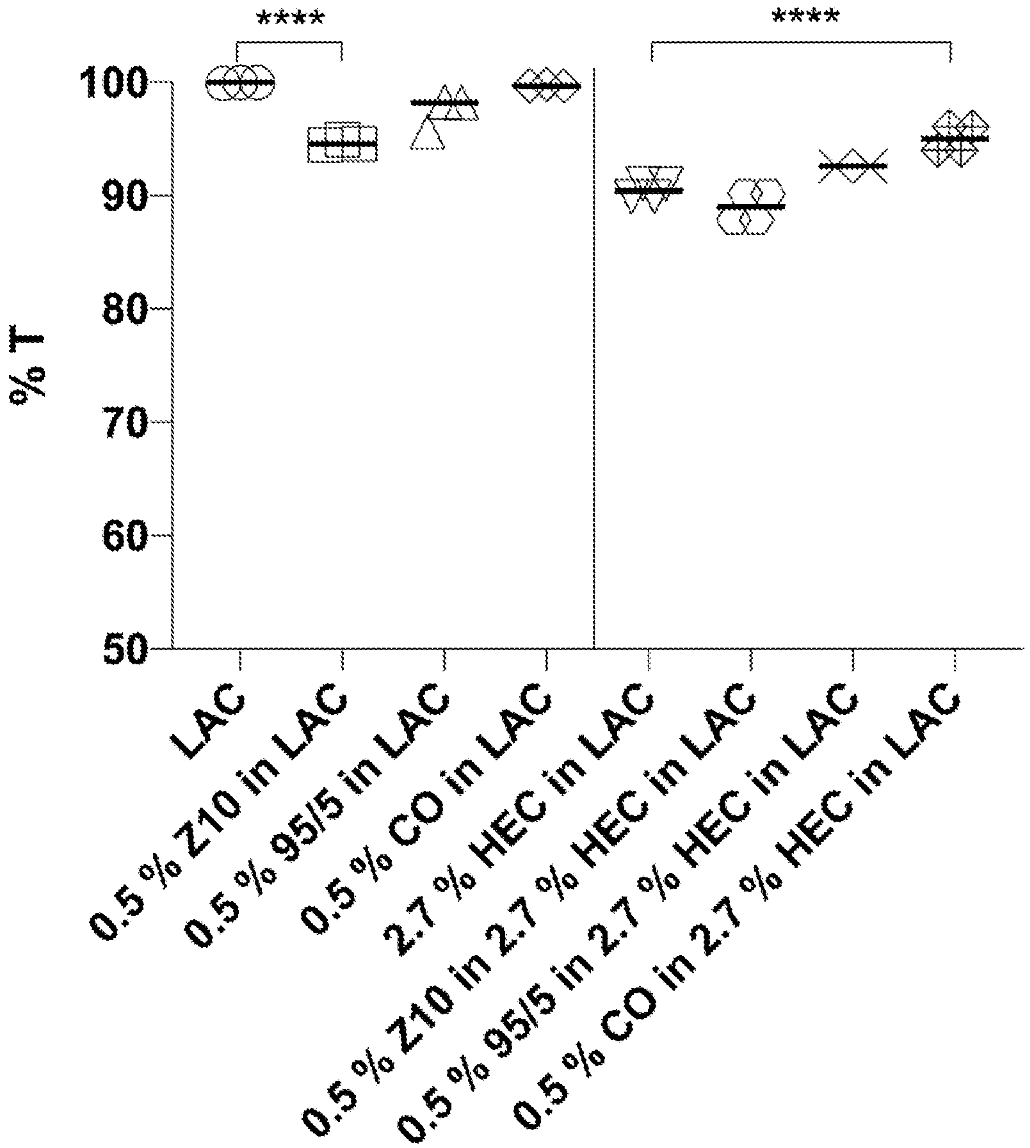

FIG. 6—Solubility test of chitosans in formulation containing thickening agents as excipients. The light transmittance (% T), or turbidity (at 600 nm) was measured for solutions of lactic acid (32.5 mM, LAC) and solution of hydroxyethylcellulose (HEC) in LAC. The molar mass of the chitosan used are corresponds to the following: Z10—36.2 kDa, 95/5-35 kDa, and CO—1.4 kDa.

Figure 7A:
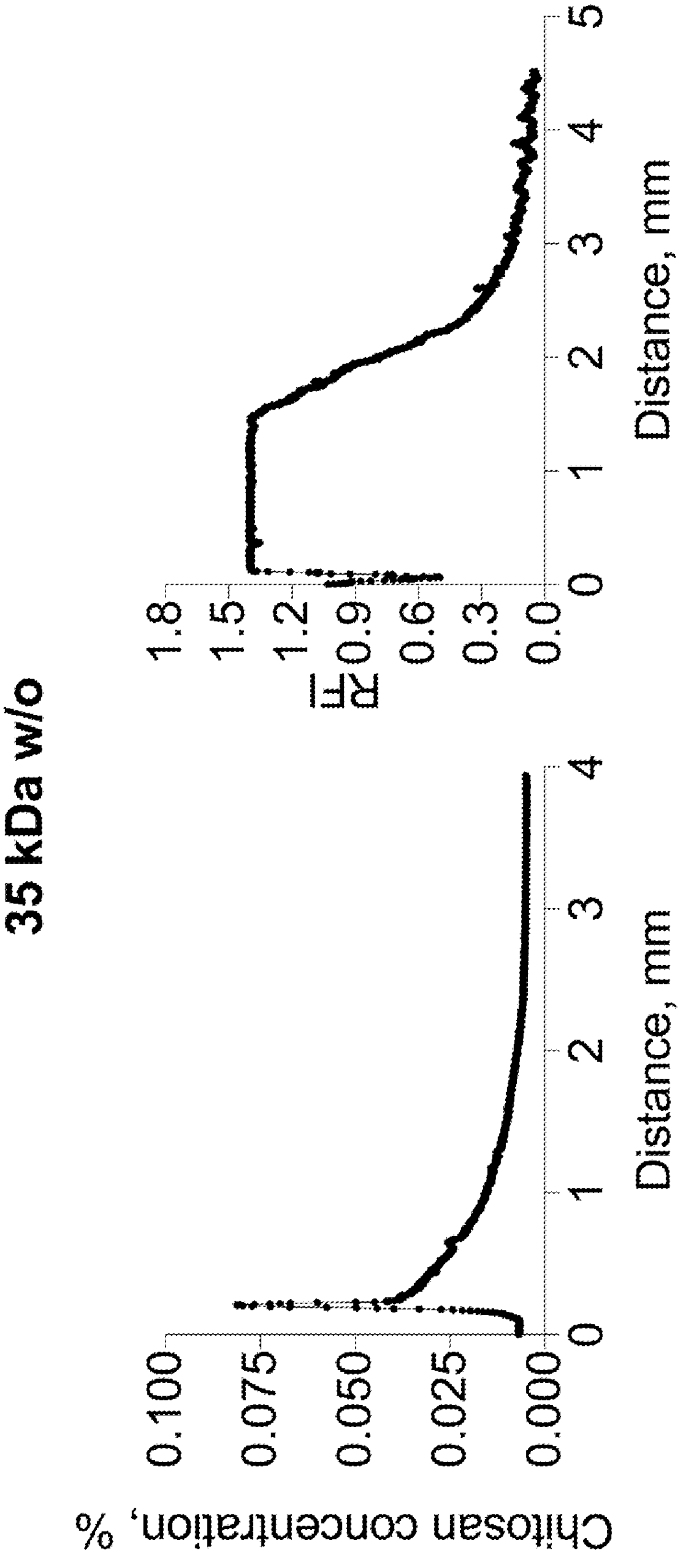
Figure 7B:
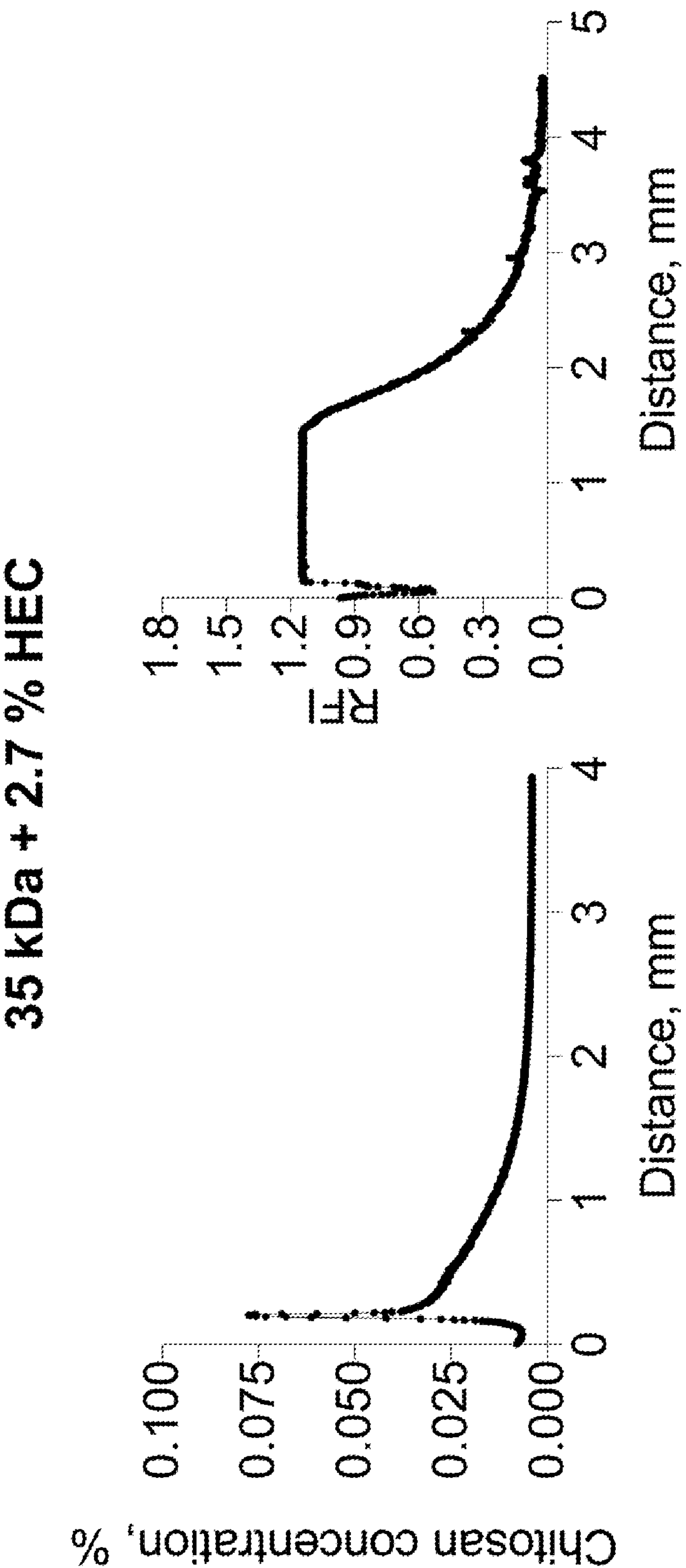
Figure 7C:
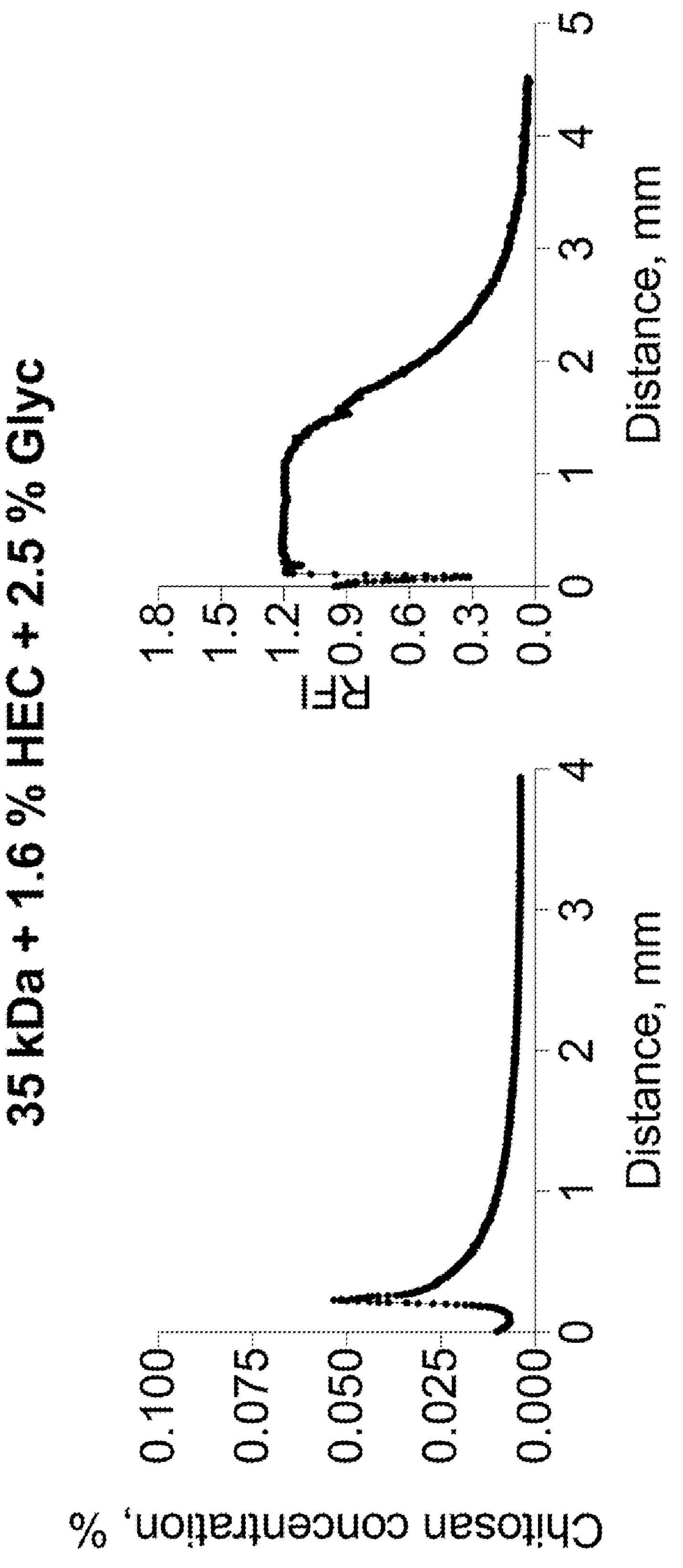

FIG. 7—Chitosan diffusion into ovulatory cervical mucus: 0.5% CS/pH 5.5 (A—35.0 kDa w/o, B—35.0 kDa+2.7% HEC, and C—35.0 kDa+1.6% HEC+2.5% Glycerol). Chitosan concentration (%, w/v) in ovulatory cervical mucus for chitosan only and chitosan blended with excipients at 20 ms after 30 min exposure. Samples were dissolved in 32.5 mM LAC. The relative fluorescence intensities (RFI) measured by microscopy with an exposure time of 800 ms. Samples were dissolved in 32.5 mM LAC. The molar mass of the chitosan used are indicated above each graph.

Figure 8A:
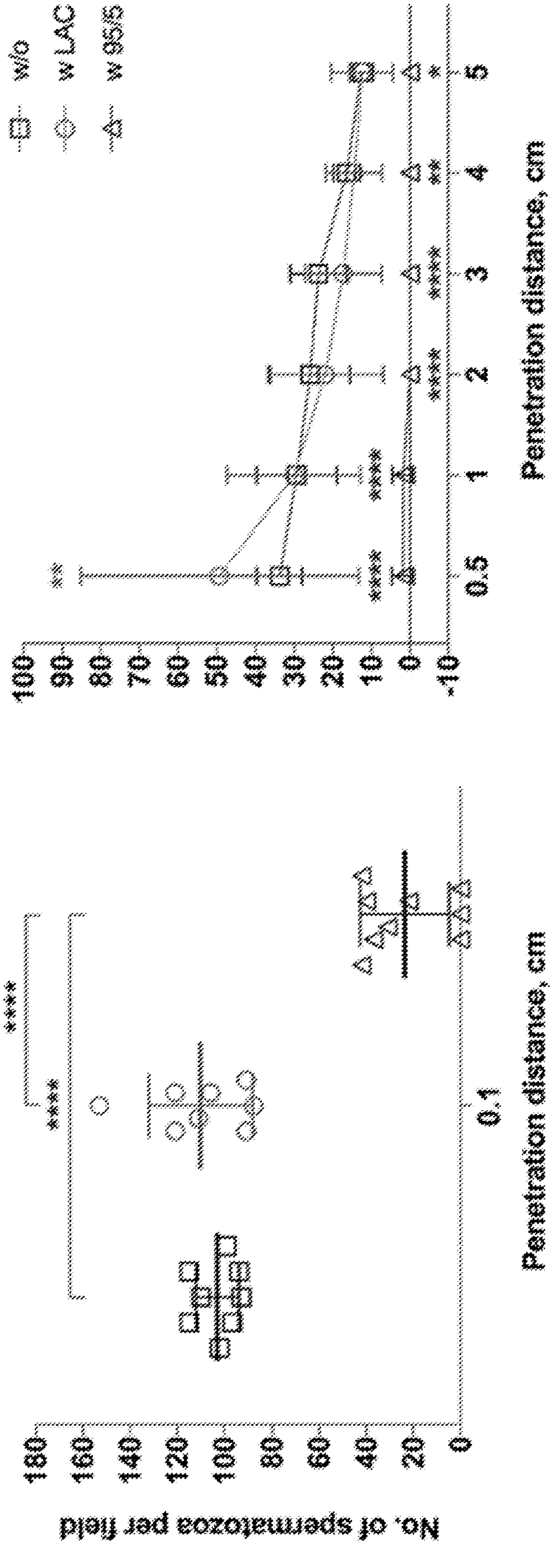
Figure 8B:
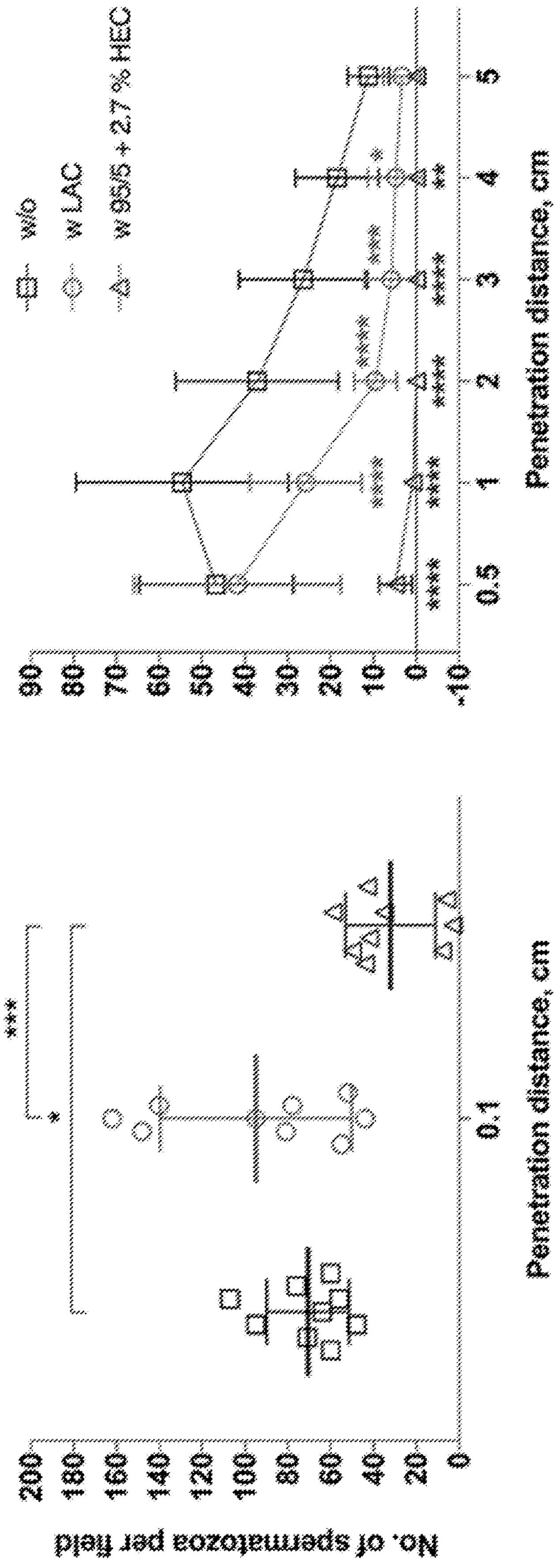
Figure 8C:
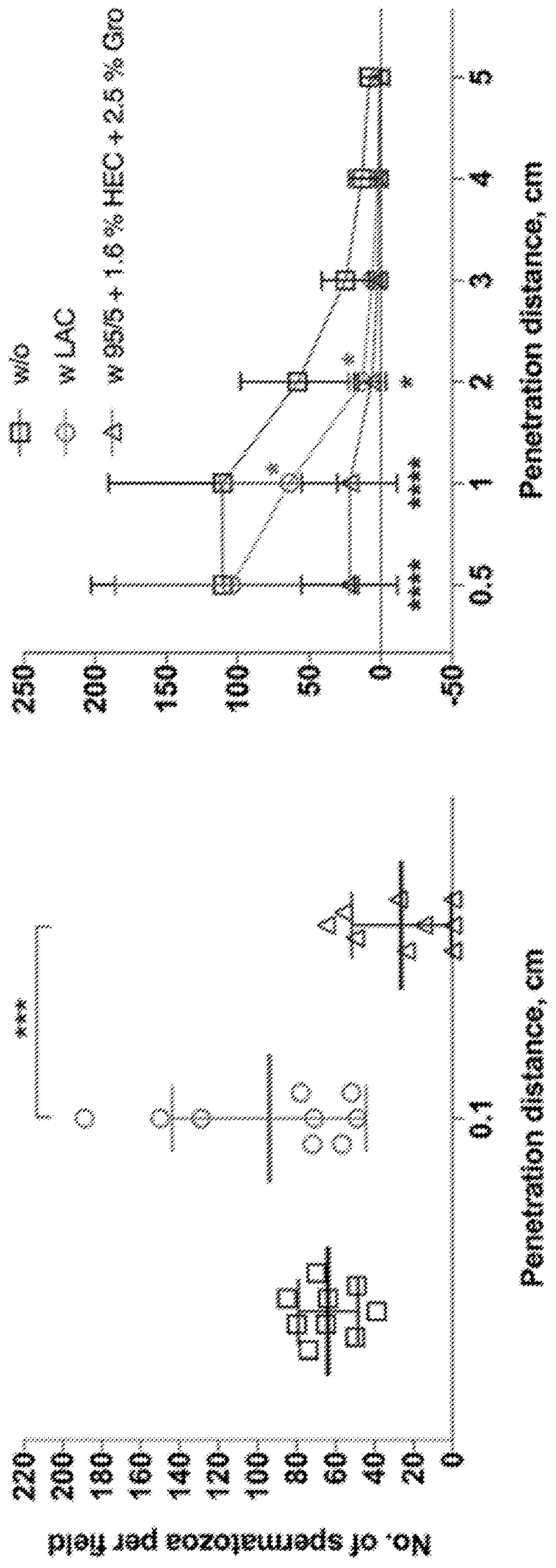

FIG. 8—Sperm penetration through human cervical ovulatory mucus. The mucus was either non treated (w/o), treated with 32.5 mM lactic acid solution (LAC), or treated with a 35 kDa crustacean shell based chitosan (95/5) dissolved in a 32.5 mM lactic acid solution (A), 32.5 mM lactic acid and 2.7% hydroxyethyl cellulose (HEC) (B), or 32.5 mM lactic acid, 2.7% hydroxyethyl cellulose and 2.5% glycerol (Gro) (C).

FIG. 9—Sperm penetration through human cervical ovulatory mucus of poly-L-lysine (PLL) (A—1.6 kDa, B—66 kDa). The mucus was either non-treated (w/o), treated with 32.5 mM lactic acid solution (LAC), or treated with either a low molar mass poly-L-lysine (A) dissolved at a concentration of 5 mg/mL in a 32.5 mM lactic acid solution or a high molar mass poly-L-lysine (B) dissolved at a concentration of 5 mg/mL in a 32.5 mM lactic acid solution.

DETAILED DESCRIPTION

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context, e.g. a composition described herein as comprising a particular element should be understood as also describing a composition consisting of that element, unless otherwise stated or clearly contradicted by context. It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined in the present specification.

As used herein, the singular forms "a," "an," and "the" are intended to include the plural forms, including "at least one," unless the content clearly indicates otherwise. "At least one" is not to be construed as limiting "a" or "an."

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

When describing the below embodiments, aspects, and definitions, the present invention envisages all disclosed embodiments and definitions in combination with all the disclosed aspects. Additionally, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

Disclosed in a first aspect of the present invention is a vaginal contraceptive composition comprising one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Disclosed in a second aspect of the present invention is the use of a vaginal contraceptive composition as a contraceptive agent, wherein said vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Disclosed in a third, fourth, and fifth aspect of the present invention is a vaginal contraceptive composition for use in therapy, for use as a contraceptive or contraceptive agent, and for use in birth control or birth control therapy, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

Disclosed in a sixth, seventh, eighth, and ninth aspect of the present invention is a method of therapy, a method of avoiding pregnancy, a method of contraception, and a method of birth control or birth control therapy, wherein the method(s) comprises the steps of using a vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

As disclosed herein, a contraceptive composition is a composition, which prevents a female from getting pregnant by preventing the spermatozoa from reaching the ovum or ova, hereby keeping the egg cell and sperm cell apart via a barrier method that may additionally help to protect against sexually transmitted infections. The spermatozoa is prevented from reaching the ovum or ova by creating a barrier at the exocervix and endocervix, hereby keeping the sperm cells in the vagina (or vaginal tract). The sperm cells will therefore never enter the uterus through the cervix and hereby have the opportunity to enter the fallopian tube (or uterine tube) to reach the egg. They are instead left to be killed by the acidic fluids inside the vagina or lost in "flow-back".

As disclosed herein, an active ingredient is one or more compounds in the contraceptive composition, which is providing the contraceptive ability, i.e. preventing a female from getting pregnant by preventing the spermatozoa from reaching the ovum or ova.

A mucoadhesive polymer is a polymer, which shows mucoadhesion. Mucoadhesion is here described as the interfacial forces that hold together two biological materials, such as the attractive forces between a biological material and mucus or a mucus membrane. By mucoadhesive polymer, is therefore meant a polymer, which has attractive force towards mucus or a mucus membrane.

Mucus is the protective cover of all epithelial surfaces, which keep the epithelial layer moist and prevent microorganism from invading the epithelium. A natural protective effect is achieved because the mucus traps microorganisms and facilitates their distal transport. When mentioning the barrier effect achieved by the mucoadhesive polymer, it is the reinforcement of the mucus due to cross-linking of the polymer. The effect of the reinforced barrier is based on the tightness of the cross-linked mucus, which stops diffusion, and how long the mucus is reinforced by the complexed mucoadhesive polymer. The latter is determined by the natural turnover of the mucus secreted by cells from the mucosa, which removes the mucus comprising the cross-linked polymer.

The mucus layer on the mucosa of the cervix differs in rheological properties depending on the four phases of the menstrual cycle. At ovulation, the cervical mucus is loose as to allow sperm passage through the gel, and therefore the pore size of the mucus will also be increased. The thickness of the barrier layer may be tailored to be impermeable to relatively large cells, such as spermatozoa, however it may also be tailored to an even tighter barrier layer, which may be required to be impermeable to bacteria, viruses, or other microorganisms or pathogens.

Given the effective barrier that the thickening of cervical mucus can form, it is well accepted that cervical mucus barrier properties can be leveraged as a contraceptive method. Indeed, the primary mechanism for contraception of the levonorgestrel intrauterine system (LNG-IUS) and progestin-only mini-pill are through to be cervical mucus thickening. The approach as disclosed in here would differ from these approaches not by the nature of the barrier, but by the mean to create the barrier: a non-hormonal, non-invasive, on demand contraceptive free from side effects.

The mucoadhesive polymer therefore provides a more reliable barrier effect, which prevents cells and microorganisms such as bacteria, viruses, and spermatozoa from penetrating the cross-linked mucus and diffuse into the mucosa membrane. The vaginal contraceptive composition may make such tight cross-linked mucus that it prevents even the smallest microorganisms from penetration, hereby not only preventing pregnancy but also sexually transmitted infections (STI).

Hence, in one or more embodiments according to any aspect, the composition is a contraceptive composition. Moreover, the invention provides a contraceptive composition free from hormones or chemicals that have undesired side effects. Undesired effects may include emboli, migraine, or minor side effects such as influencing the menstrual cycle. The effective time of the mucoadhesive polymer according to the invention is determined by the turnover of mucus, which means that the contraceptive effect is temporary. The contraception dissolves after the effective time and the fertility is unaffected. The time of sufficient contraception is affected by several factors such as the biological turnover of the mucus, the concentration of mucoadhesive polymer etc. The contraceptive effect last fora period of time, such as 1, 2, 3, 4, 5, 6, 7, 8, 9, 10 hours, 1, 2, 3 day(s) or even up to 10 days, which is a sufficient time to block sperm cells from entering the cervix. By blocking the sperm from entering the cervix, the acidic environment of the vagina will reduce the motility of the sperm and weaken the sperm leaving them unable to fertilise an egg. Under natural conditions, the sperm cells will need to enter the cervix within minutes to survive. The full contraceptive effect is gained from a single application, which means that non-coherent use of the contraceptive composition gives the same protection as coherent use. That the full contraceptive effect is gained from a single application may also mean that temporary contact of the cervical mucus with the contraceptive composition may give the same full protection as the continued contact with the cervical mucus.

The size of the mucoadhesive polymer allows the molecule to diffuse inside the mucus. This diffusion of the mucoadhesive polymer into the mucus membrane allows that it can cross-link the mucus layer over a large thickness sufficiently to prevent motile sperm from movement through the mucus, without aggregating the mucus. The mucoadhesive polymers complex to the mucus thereby blocking the pores of the network and reinforcing its barrier properties. At ovulation, the cervical mucus is loose as to allow sperm passage through the gel, and therefore the pore size of the mucus will also be increased as comparted with non-ovulatory mucus. The size of the mucoadhesive polymer should therefore be tailored towards this increased pore size of ovulatory cervical mucus. A size of the mucoadhesive polymer working for the increased pore size of ovulatory cervical mucus is also effectively working when the pore size of the cervical mucus is not increased due to ovulation.

Moreover, the size of the mucoadhesive polymers are generally more soluble at lower molecular weight, and has less steric hindrance. If the mucoadhesive polymer is large it may not pass, or fit, through the pores of the mucus and it will therefore end up interacting with and increased number of mucin molecules hereby not diffusing through the gel, but if it is too small, it may pass straight through without interacting with any mucin molecules. Hence, a compromise between a larger size, but not too large, to avoid the mucoadhesive polymer to penetrate all the way through the pore of the mucus, and a smaller size to obtain a high enough solubility for appropriate delivery to a mucus membrane of a subject is needed. Hereby, the mucoadhesive polymer can be delivered more efficiently to the mucus membrane, which in turn allows a stronger, and thus more effective, cross-linking than is available using smaller or larger mucoadhesive polymer molecules (below 20.000 Da or above 100.000 Da).

The mucoadhesive polymer is generally cationic with at least 50% of the monomers being charged. The monomer units may e.g. comprise amino groups, which at physical pH is positively charged. It may also be hydrophobic, e.g. with up to 50% of the monomers having a hydrophobic side chains. These two features of the mucoadhesive polymer may play a roll, if selecting a compatible excipient.

Amino groups, in chemistry, are functional groups that consists of a nitrogen atom attached by single bonds to hydrogen atoms, alkyl groups, aryl groups, or a combination of these three. An organic compound that contains an amino group is called an amine. Amines are derivatives of the inorganic compound ammonia, $NH_3$. When one, two, or all three of the hydrogens in ammonia are replaced by an alkyl or aryl group, the resulting compound is known as a primary, secondary, or tertiary amine, respectively. Like ammonia, the amines are weak bases because the unshared electron pair of the nitrogen atom can form a coordinate bond with a proton. A water-insoluble amine can be made dissolvable by adding acid to form its water-soluble amine salt. The amino groups make the mucoadhesive polymer basic, which is advantageous for their binding to the mucus membrane because of the large amount of negatively charged molecules is contains. The basic amino groups particularly provide a more efficient cross-linking. In addition, when some of the monomers of the mucoadhesive polymer, up to 50%, comprise a hydrophobic group, the mucoadhesive polymer can also adhere to and diffuse into the mucus membrane to cross-link the mucus membrane without aggregating the mucus. In the context of the invention, an amino group is —$NH_2$, where one or both hydrogen atoms may be substituted with a group R, or the amino group may be a quaternary amino group with three R groups, i.e. —$N^+R_3$. R may be selected from C1-C4 alkyls, optionally substituted with one or more —OH, —SH, or —$NH_2$. When more than one R is present on the same nitrogen atom these may be the same or different R groups. As long as R has four or fewer carbon atoms, and in particular when hydrogen atoms of the R groups are substituted by one or more —OH, —SH, or —$NH_2$, the amino groups as disclosed herein are generally seen as being basic. Longer alkyl chains, e.g. having five or more carbon atoms, may mask the basicity of the amino group, however, amino groups carrying alkyls of five or more carbon atoms are still counted as amino groups in the context of the present invention. Likewise, the sugar may also comprise an amide group, e.g. —$CONHCH_3$, or —NHCHO, but such groups are not counted as amino groups in the context of the invention.

In one or more embodiments according to any aspect, the amino groups do not comprise alkyls of ten or more carbon atoms.

In one or more embodiments according to any aspect, the amino groups do not comprise alkyls of nine or more carbon atoms.

In one or more embodiments according to any aspect, the amino groups do not comprise alkyls of eight or more carbon atoms.

In one or more embodiments according to any aspect, the amino groups do not comprise alkyls of six or more carbon atoms.

In one or more embodiments according to any aspect, the amino groups do not comprise alkyls of five or more carbon atoms.

In one or more embodiments according to any aspect, at least 55% of the monomer units, such as at least 60% of the monomer units, such as at least 65% of the monomer units, such as at least 70% of the monomer units comprise at least one amino group.

In one or more embodiments according to any aspect, one or more of the at least one amino group is a primary amine. In the context of the invention, a primary amine is an amino group without any hydrogen atoms being substituted with a group R substitution (i.e. —$NH_2$).

In one or more embodiments according to any aspect, the at least one amino group is a primary amine.

The vaginal contraceptive composition comprises one or more active ingredients and a physiological acceptable gelling agent. The one or more active ingredients may be administered in a physiologically acceptable gelling agent (or carrier), which ensures that the one or more active ingredients are soluble in the conditions where it is used and ensures that the one or more active ingredients are evenly distributed in the target area. Here evenly distributed means that the targeted mucus area is subjected to at least a minimum amount of composition with enough active ingredient to diffuse into the mucus and reinforce the mucus barrier.

By physiological acceptable gelling agent (or carrier) is meant a non-toxic compound, which in an effective dose, is neither chemically nor physically toxic to a human and/or animal organism.

In one or more embodiments according to any aspect, the physiological acceptable gelling agent is selected from hydroxyethyl cellulose (HEC), glycerol, hydroxypropylmethyl cellulose (HPMC), hydroxypropyl cellulose, guar gum, or combinations hereof. Any suitable pharmaceutical gelling agent may be used as long as the gelling agent does not interact with the one or more active ingredients, especially the mucoadhesive polymer.

By combination with a physiological acceptable gelling agent, the contact area between the composition and the mucus is maximised. Increased contact area may help ensure that a maximum amount of mucoadhesive polymer can diffuse into the mucus layer and modify its properties. Also contributing to the increased diffusion is a high density of the composition. By having a high composition density, e.g. similar to that of water, such as in a semi-solid gel, the applied composition is able to change shape and envelope the full surface of the cervical entrance.

Hydroxyethyl cellulose (or ethyl cellulose) is a gelling and thickening agent derived from cellulose. It is widely used in cosmetics, cleaning solutions, and other household products. Hydroxyethyl cellulose and hydroxymethyl cellulose (or methyl cellulose) are frequently used with hydrophobic drugs in capsule formulations, to improve the drugs' dissolution in the gastrointestinal fluids. This process is known as hydrophilization.

In one or more embodiments according to any aspect, the physiological acceptable gelling agent is selected from hydroxyethyl cellulose, hydroxymethyl cellulose, or combinations hereof.

Glycerol, also called glycerine or glycerin, is a simple polyol compound. It is a colourless, odourless, viscous liquid, which is sweet tasting and non-toxic. The glycerol backbone is found in many lipids, which are known as glycerides. It is widely used in the food industry as a sweetener and humectant in pharmaceutical formulations. Glycerol has three hydroxyl groups that are responsible for its solubility in water and its hygroscopic nature.

In one or more embodiments according to any aspect, the physiological acceptable gelling agent is glycerol.

Hydroxypropyl methylcellulose (HPMC), also called hypromellose, is a semisynthetic, inert, viscoelastic polymer used as eye drops, as well as an excipient and controlled-delivery component in oral medicaments, found in a variety of commercial products. As a food additive, hypromellose is an emulsifier, thickening, and suspending agent, and an alternative to animal gelatine. Its Codex *Alimentarius* code (E number) is E464.

In one or more embodiments according to any aspect, the physiological acceptable gelling agent 40 is hydroxypropylmethyl cellulose (HPMC).

Hydroxypropyl cellulose (HPC) is a derivative of cellulose with both water solubility and organic solubility. It is used as an excipient, and topical ophthalmic protectant and lubricant. HPC is an ether of cellulose in which some of the hydroxyl groups in the repeating glucose units have been hydroxypropylated forming —$OCH_2CH(OH)CH_3$ groups using propylene oxide. The average number of substituted hydroxyl groups per glucose unit is referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3.

In one or more embodiments according to any aspect, the physiological acceptable gelling agent is hydroxypropyl cellulose.

Guar gum, also called guaran, is a galactomannan polysaccharide extracted from guar beans that has thickening and stabilizing properties useful in the food, feed, and industrial applications. The guar seeds are mechanically dehusked, hydrated, milled, and screened according to application. It is typically produced as a free-flowing, off-white powder. Chemically, guar gum is an exo-polysaccharide composed of the sugars galactose and mannose. The backbone is a linear chain of β 1, 4-linked mannose residues to which galactose residues are 1, 6-linked at every second mannose, forming short side-branches. Guar gum has the ability to withstand temperatures of 80° C. for five minutes.

In one or more embodiments according to any aspect, the physiological acceptable gelling agent is guar gum.

In one or more embodiment according to any aspect, the pharmaceutical acceptable gelling agent is a pharmaceutical acceptable carrier, wherein the pharmaceutical acceptable carrier may be water, dimethyl sulfoxide (DMSO), saline (saline solution), or a combination thereof.

In one or more embodiments according to any aspect, the vaginal contraceptive composition is not a foam.

A foam is an object formed by trapping pockets of gas in a liquid or solid. In most foams, the volume of gas is large, with thin films of liquid or solid separating the regions of gas.

The mucoadhesive polymer may be a polysaccharide where C6 sugars are linked to each other via ether, ester, or amide bonds. The monomers of C6 sugars may be linked via e.g. any ether bond, e.g. $C_1$ and $C_4$ of two adjacent C6 sugars may be linked, or $C_1$ and C6 of two adjacent $C_6$ sugars may be linked. In particular, when the monomer is a C6 sugar, e.g. glucose, the monomers, e.g. glucose monomers, may be linked via β 1, 4-linkages.

The at least one amino group may be linked to any carbon atom of the glucose monomers, e.g. $C_2$ or $C_3$.

In one or more embodiments according to any aspect, the mucoadhesive polymer consists of a plurality of monomer units linked to each other via ether bonds.

In one or more embodiments according to any aspect, the monomer units are selected from C6 sugars, amino-functionalised C6 sugars, or combinations hereof.

C6 sugars are carbohydrates whose molecules have six carbons (i.e. hexoses). The best-known example of this class is glucose, a principal component of cellulose and starch molecules.

An amino-functionalized C6 sugar (or amino sugar) is a sugar molecule in which a hydroxyl group has been replaced with an amine group. More than 60 amino sugars are known, with one of the most abundant being N-acetyl-D-glucosamine, which is the main component of chitin. The amino-functionalization may be on the $C_2$, $C_3$, $C_4$, and/or $C_5$ of the C6 sugar.

In one or more embodiments according to any aspect, the monomer units are amino-functionalised C6 sugars.

In one or more embodiments according to any aspect, the monomer units are a combination of D-glucosamine and N-acetyl-D-glucosamine.

D-glucosamine ($C_6H_{13}NO_5$) is an amino sugar and a prominent precursor in the biochemical synthesis of glycosylated proteins and lipids. D-Glucosamine is part of the structure of the polysaccharides, chitosan, and chitin. D-Glucosamine is one of the most abundant monosaccharides. It is produced commercially by the hydrolysis of crustacean exoskeletons or, less commonly, by fermentation of a grain such as corn or wheat.

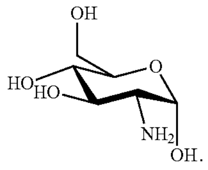

Structure of D-glucosamine

N-Acetyl-D-glucosamine (GlcNAc, $C_6H_{15}NO_6$) is a monosaccharide and a derivative of glucose. It is significant in several biological systems. It is part of a biopolymer in the bacterial cell wall, which is built from alternating units of GlcNAc and N-acetylmuramic acid (MurNAc), cross-linked with oligopeptides at the lactic acid residue of MurNAc. This layered structure is called peptidoglycan (formerly called murein). GlcNAc is the monomeric unit of the polymer chitin, which forms the outer coverings of insects and crustaceans.

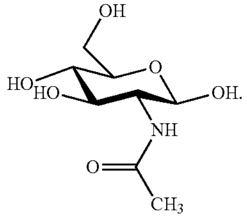

Structure of N-acetyl-D-glucosamine

In one or more embodiments according to any aspect, at least 50% of the monomer units is D-glucosamine whereas 50% or less of the monomer units is N-acetyl-D-glucosamine, such as between 50% and 100% is D-glucosamine and between 0% and 50% is N-acetyl-D-glucosamine.

By at least 50% of the monomer units is D-glucosamine is meant that at least 50% of the total amount of monomers in the mucoadhesive polymer is from D-glucosamine. Similarly, by 50% or less of the monomer units is N-acetyl-D-glucosamine is meant that 50% or less of the total amount of monomers in the mucoadhesive polymer is from N-acetyl-D-glucosamine. Further, by between 50% and 100% or between 0% and 50% is meant that between 50% and 100% or between 0% and 50% of the total amount of monomers in the mucoadhesive polymer is from said monomer unit, all end-points are included (0%, 50%, and 100%).

In one or more embodiments according to any aspect, at least 65% of the monomer units is D-glucosamine whereas 35% or less of the monomer units is N-acetyl-D-glucosamine, such as between 65% and 100% is D-glucosamine and between 0% and 35% is N-acetyl-D-glucosamine. End-points are included.

In one or more embodiments according to any aspect, the mucoadhesive polymer is chitosan where at least 50% of the glucose monomers have an —$NH_2$ group. The chitosan may also be referred to as at least 50% deacetylated.

Chitosan is a linear polysaccharide composed of randomly distributed β 1, 4-linked D-glucosamine (deacetylated unit) and N-acetyl-D-glucosamine (acetylated unit). It is made by treating the chitin shells of shrimp and other crustaceans with an alkaline substance, like sodium hydroxide, or it can be extracted from other sources such as fungal cell walls.

When the mucoadhesive polymer is chitosan it is important to avoid e.g. the presence of high molecular weight polyacrylic acids, as the carboxyl functional groups in the acrylic monomers form ionic complexes with the basic amino groups in the chitosan chain, which leads to the formation of a highly swollen interpenetrating polymeric network. This will result in aggregation of the mucus thus results in opening of pores within the mucus and causes a weakening of the barrier properties of the mucus.

Chitosan is a strongly mucoadhesive molecule, meaning that it is able to entangle with and bind to the mucin glycoproteins that compose the mucus gels. As such, they have been used in mucosal drug delivery devices and are included in commercial hemostatic products. However, chitosan used as disclosed herein is typically of high molar mass, and thus diffuse poorly within the mucus gel and tend to aggregate and compact the mucus.

In one or more embodiments according to any aspect, the mucoadhesive polymer is chitosan where at least 50% of the glucose monomers have an $-NH_2$ group, and where 40% or less of the glucose monomers have a $-CONHCH_3$ group.

In one or more embodiments according to any aspect, the mucoadhesive polymer is chitosan where at least 50% of the glucose monomers have an $-NH_2$ group, and where 20% or less of the glucose monomers have a $-CONHCH_3$ group.

In one or more embodiments according to any aspect, the mucoadhesive polymer is chitosan where at least 70% of the glucose monomers have an $-NH_2$ group. The chitosan may also be referred to as at least 70% deacetylated.

In one or more embodiments according to any aspect, the mucoadhesive polymer is chitosan where at least 70% of the glucose monomers have an $-NH_2$ group, and where 20% or less of the glucose monomers have a $-CONHCH_3$ group.

In one or more embodiments according to any aspect, the mucoadhesive polymer is selected from chitosan, chitosan-trimethyl, chitosan-thioglycolic acid, chitosan-iminothiolane, chitosan-thioethylamidine, or combinations hereof.

Chitosan-trimethyl is a quaternized hydrophilic derivative of chitosan. This quaternized derivative of chitosan possesses a positive charge and is soluble over a wide range of pH.

Chitosan-thioglycolic acid, chitosan-iminothiolane, and chitosan-thioethylamidine are chitosan-derivatives, which have been modified by the introduction of different thiol groups. The thiol groups are introduced to chitosan via amide bond formation mediated by a carbodiimide. The properties of the resulting polymer is hereby altered in regard to water solubility, mucoadhesion, biodegradability and in situ gelling compared to the original polymer.

In one or more embodiments according to any aspect, the mucoadhesive polymer is chitosan which has a molecular weight between 20.000 Da and 100.000 Da, such as between 30.000 Da and 90.000 Da, such as between 30.000 Da and 80.000 Da, such as between 30.000 Da and 70.000 Da, such as between 40.000 Da and 60.000 Da, such as a molecular weight between 45.000 Da and 55.000 Da. All end-points are included in the above ranges.

In one or more embodiments according to any aspect, the mucoadhesive polymer is a peptide molecule of a length of 180 to 900 amino acids, which are linked via amide bonds. When the mucoadhesive polymer comprises amino acids, any amino acid may be included as long as at least 50% of the amino acids carry a basic group, or as long as at least 50% of the amino acids carry a hydrophobic group as appropriate, or as long as at least 50% of the amino acids carry thiol groups, or a combination of these three (basic, hydrophobic, and thiol). The mucoadhesive polymer is not limited to naturally occurring amino acids, but it is preferred that the amino acids are non-toxic and tolerated by the subject. It is preferred that the mucoadhesive polymer does not comprise D-amino acids but that any amino acid contained in the mucoadhesive polymer is an L-amino acid.

In general, the following amino acids are considered basic: arginine, lysine, histidine, ornithine, and β-alanine, and in an embodiment the mucoadhesive polymer is a polypeptide of amino acids, wherein at least 50% of the amino acids are selected from the list consisting of arginine, lysine, histidine, ornithine, and 6-alanine. The remaining amino acids may be selected from any amino acids, e.g. any of the 20 amino acids defined from the genetic code, but in particular glycine, serine, threonine, asparagine, and glutamine. Specific embodiments of the mucoadhesive polymer comprise poly-lysine, poly-orthinine, and/or poly-arginine. The advantage of using basic amino acids is that they have a good solubility in aqueous solutions.

In one or more embodiments according to any aspect, the mucoadhesive polymer is a peptide molecule of a length of 180 to 900 amino acids wherein at least 50% of the amino acids carry a hydrophobic group, which amino acids are selected from the list consisting of: alanine, methionine, cysteine, phenylalanine, leucine, valine, and isoleucine. The remaining amino acids may be selected from the list consisting of: glycine, serine, threonine, asparagine, and glutamine, or the remaining amino acids may be selected from any amino acids, e.g. any of the 20 amino acids defined from the genetic code.

In one or more embodiments according to any aspect, the mucoadhesive polymer comprises amino acids, wherein at least 50% of the amino acids are selected from the group consisting of arginine, lysine, histidine, ornithine, and 6-alanine, or 50% of the amino acids carries a hydrophobic group, and are selected from the group consisting of alanine, methionine, cysteine, phenylalanine, leucine, valine, and isoleucine.

In one or more embodiments according to any aspect, the mucoadhesive polymer is a peptide molecule, which are linked via amide bonds, wherein at least 50% of the amino acids are selected from the list consisting of arginine, lysine, histidine, ornithine, and β-alanine. In another embodiment, at least 60% of the amino acids are selected from the list consisting of arginine, lysine, histidine, ornithine, and β-alanine. In yet another embodiment, at least 70% of the amino acids are selected from the list consisting of arginine, lysine, histidine, ornithine, and β-alanine.

In one or more embodiments according to any aspect, the mucoadhesive polymer is a peptide molecule, which are linked via amide bonds, wherein at least 50% of the amino acids are lysine. In another embodiment, at least 60% of the amino acids are lysine. In yet another embodiment, at least 70% of the amino acids are lysine.

In one or more embodiments according to any aspect, the mucoadhesive polymer comprises amino acids being L-lysine. In one or more embodiments according to any aspect, the mucoadhesive polymer is poly-L-lysine (PLL).

It is advantageous to use amino acids or hydrophobic amino acids since they are biodegradable. The protein-peptide interactions between the mucus proteins and the polymer may enhance mucoadhesion. Furthermore, the amino acid polymers may be produced recombinant using bacteria or synthetically.

In one or more embodiments according to any aspect, the mucoadhesive polymer comprises both sugar monomers, e.g. C6 sugar monomers, and amino acids, wherein at least 50% of the monomers are basic, e.g. carry an amino group, or at least 50% of the monomers are hydrophobic, e.g. carry a hydrophobic group.

In one or more embodiments according to any aspect, the mucoadhesive polymer consists of 40 to 800 monomer units linked to each other via ether bonds, ester bonds, amide bonds, or combinations hereof, such as 50 to 750 monomer units, such as 75 to 700 monomer units, such as 100 to 650 monomer units, such as 150 to 600 monomer units linked to each other via ether bonds, ester bonds, amide bonds, or combinations hereof. The size of the mucoadhesive polymer is very important as it ensures that the polymer is small enough to diffuse deep into the mucus gel and large enough to form a tight cross-linking network. By tight is meant e.g., impermeable to microorganism or sperm cells.

In one or more embodiments according to any aspect, the mucoadhesive polymer is selected 35 from polymers with a low molecular weight, which should have a degree of polymerisation (DP) providing a molecular weight in the range of 20 to around 100 kDa, which ensures that the mucoadhesive polymer forms stable complexes with the mucus.

In one or more embodiments according to any aspect, the mucoadhesive polymer has a 40 molecular weight between 20.000 Da and 90.000 Da, such as between 30.000 Da and 80.000 Da, such as between 30.000 Da and 70.000 Da, such as between 40.000 Da and 60.000 Da, such as a molecular weight between 45.000 Da and 55.000 Da. All end-points are included in the above ranges.

The size or the polymer ensures that the polymer is soluble in the conditions used, and that the polymer can diffuse through the pores of mucus and form a thick and tight barrier.

The mucoadhesive polymer should be stable in the environment of the targeted mucosa, which is low pH in the female abdomen. The pH range where the mucoadhesive polymer is stable is therefore in the range of 1-8. Dependent on the pH environment, different types and sizes of polymers may be used.

In one or more embodiments according to any aspect, pH of the vaginal contraceptive composition is between 2.0 and 7.0, such as between 2.5 and 6.5, such as between 3.0 and 6.0. All end-points are included in the above range.

By a pH of the composition between 2.0 and 7.0 is meant that the pH, if measured, is between the two values and that the mucoadhesive polymer is stable in this range. A lower pH of the composition is preferable if the compositions are to be applied to the female abdomen, especially to the female vagina, where pH value is ranging from 3 to 5.

The diffusion of the mucoadhesive polymer occurs when the mucoadhesive polymer and a physiologically acceptable gelling agent adheres to the mucus. The use of the mucoadhesive polymers in therapy is possible due to its degree of polymerisation and degree of acetylation, which gives good mucoadhesion. This allows the polymer to diffuse into the mucus and temporarily block the pores of the mucus. This occurs due to a temporary cross-linking effect of the mucus, which is controlled by the normal turnover of mucus and the biodegradability of the mucoadhesive polymer. The effective cross-linking time can therefore be adjusted by subjecting the mucus to different concentrations of the mucoadhesive polymer such as for example a concentration from 1 mg/mL to 100 mg/mL, such as a concentration from 1 mg/mL to 75 mg/mL, such as a concentration from 1 mg/mL to 50 mg/mL, such as a concentration from 1 mg/mL to 25 mg/mL, such as a concentration in the range of 5 mg/mL. All end-points are included in the above ranges.

In one or more embodiments according to any aspect, the mucoadhesive polymer is in a concentration of between 0.05 wt. % and 10.0 wt. % of the total weight of the vaginal contraceptive composition, such as between 0.5 wt. % and 10.0 wt. %, such as between 1.0 wt. % and 10.0 wt. %, such as between 2.5 wt. % and 10.0 wt. %, such as between 5.0 wt. % and 10.0 wt. %, such as between 0.05 wt. % and 10.0 wt. %, such as between 0.05 wt. % and 8.0 wt. %, such as between 0.05 wt. % and 6.0 wt. %, such as between 0.05 wt. % and 4.0 wt. % of the total weight of the vaginal contraceptive composition.

By between 0.05 wt. % and 10.0 wt. % is meant that between 0.05% and 10.0% of the total weight of the vaginal contraceptive composition is from the mucoadhesive polymer. All end-points are included in the above ranges.

The mucoadhesive polymer will, due to its adhesive properties and size, penetrate the mucus and diffuse into the surface of the mucus to form a thick layer. The mucoadhesive polymer will then complex to the mucus and thereby block the pores of the network, providing a reinforced-barrier property to the mucus. When the mucus is reinforced, it is impermeable to particles, and prevents passage e.g. externally induced liquids, particles and cells, such as spermatozoa. The complex formed in the mucus could be targeted against a certain size of cells, and thereby be impermeable to virions (or viruses) of the range of 20 to 30 nm in size, *mycoplasma* in the range of 0.3 microns, bacteria in the range of 0.5 to 5 microns, or spermatozoa in the range of 3 microns.

The composition of the invention comprising a mucoadhesive polymer and a pharmaceutical acceptable gelling agent as a contraceptive agent, since the treated mucus will be temporarily impermeable to spermatozoa. The contraceptive effect in connection with the present invention means a reversible and temporary prevention of pregnancy due a non-surgical and hormone-free barrier effect achieved by a single use, meaning that the contraceptive effect is achieved by one application, and does not require a concentration to be developed over a period of time, as it does with e.g. hormone pills such as a combined oral contraceptive pill (often referred to as the birth control pill or colloquially as "the pill").

By temporary effect is implied that, when applied to the mucus, the effect of the mucoadhesive polymer is reversible. The rate at which the reversion will occur is determined by the amount of polymer diffused into the mucus and by the biological turnover of the mucus itself.

In another aspect, the invention is a kit of parts, which comprises the vaginal contraceptive composition comprising the mucoadhesive polymer and the physiological acceptable gelling agent, e.g. a contraceptive composition as described above, and an applicator. In one embodiment, the applicator is a delivery device utilising a method where the applicator comprising the vaginal contraceptive composition in the form of a gel, which is inserted in the vagina via a syringe or by introduction of a soft-gel capsule that dissolves in the vagina, releasing the gel. The gel is deployed from the applicator and applied to the cervical mucus; hereby the mucus is cross-linked by the mucoadhesive polymer. In an embodiment, the applicator is a container, which contains the vaginal contraceptive composition, and which can be emptied by an emptying mechanism.

The composition comprising the mucoadhesive polymer and a physiological acceptable gelling agent may be part of a kit further comprising an applicator. The applicator may be used to apply the composition to the surface of e.g. the cervix.

In one embodiment, the applicator is a syringe. In another embodiment, the applicator is a soft-gel capsule.

In a further embodiment, the kit comprises the vaginal contraceptive composition, an applicator, and instructions for use.

A vaginal contraceptive composition according to any embodiment may be used at any time of day, ahead of intercourse. Preferably, between 24 hours to 30 seconds before intercourse. The vaginal contraceptive composition may be used with the intention to prevent pregnancy and it may be administered in an amount of between 1 to 5 mL by vaginal administration, using either a syringe or a soft-gel capsule. The vaginal contraceptive composition is to be inserted vaginally, either using fingers or an applicator.

The present invention is further illustrated by the following examples, which are not to be construed as limiting the scope of protection. The features disclosed in the foregoing description and in the following examples may, both separately or in any combination thereof, be material for realizing the invention in diverse forms thereof.

Various examples are described hereinafter with reference to the figures. It should also be noted that the figures are only intended to facilitate the description of the examples. They are not intended as an exhaustive description of the claimed invention or as a limitation on the scope of the claimed invention. In addition, an illustrated example needs not have all the aspects or advantages shown. An aspect or an advantage described in conjunction with a particular example is not necessarily limited to that example and can be practiced in any other examples even if not so illustrated, or if not so explicitly described.

EXAMPLES

Inhere it is shown that the hydrogels of porcine gastric mucin and the mucus layer produced by colonic cell lines could be altered by low molar mass chitosan (below 2.000 Da), which would reinforce the barrier properties and slows the diffusion of dextran polymers and a subunit of the cholera toxin through the hydrogels.

Although all mucus gels share similar characteristics, they also differ by a number of ways. This includes mucin contraction (e.g. pore size), mucin concentration and type of associated protein and lipids, and salt concentration. Additionally, they also differ in environmental factors such as pH, exposure to shear stress, exposure to bacteria, and different turnover rates. Given these differences, it is therefore not obvious that a treatment designed for porcine mucin hydrogels would also work in reinforcing the barrier properties of cervical mucus.

Example 1

We performed experiments using a range of chitosans types varying mostly in the molar mass and the tissue origin (animal vs fungi) from which they were extracted to test the capacity of the chitosan to interact and diffuse within human ovulatory cervical mucus, and their capacity to increase the barrier of human ovulatory cervical mucus to human sperm.

Materials and Methods

Chitosan Labelling

Chitosans (CS) and chitosan oligomers (CO) were labelled by fluorescein isothiocyanate (FITC) (Sigma-Aldrich), using a modified method previously reported in Kootala et al. 2018 (Kootala, Sujit, Luimar Filho, Vaibhav Srivastava, Victoria Linderberg, Amani Moussa, Laurent David, Stephane Trombotto, and Thomas Crouzier. 2018. "Reinforcing Mucus Barrier Properties with Low Molar Mass Chitosans." Biomacromolecules 19 (3): 872-82). Briefly, chitosan of 40 mg/ml in 2 ml lactic acid solution (pH 5) was prepared, 2 ml methanol was added, and the mixture was treated with 2M HCl or 2 M NaOH to adjust the pH to 5.5. Then, a solution of 10 mg/ml FITC in DMSO was added to achieve a ratio of 1:50 (1 fluorescein for every 50 monomers) followed by 2 h of shaking at room temperature in the dark. Chitosans were precipitated by the successive addition of 2 mL of 2 M NaOH to increase the pH to 9 in addition to 10 ml ethanol. The supernatant was removed after centrifugation at 20,000×g for 25 min at 4° C. The pellet was then rinsed three times to extract unconjugated FITC each time by re-suspending the pellet in ethanol, then centrifugation at 20,000×g for 10 min at 4° C. and removing the supernatant. After removing ethanol by rotor vaporization for 2 h, the pellet was frozen with liquid nitrogen, lyophilized and stored at 4° C.

TABLE 1

Characteristics of the chitosans used.

| Chitosan (Identification name) | DDA (%) | Mw (kDa) |
|---|---|---|
| ZXP1 | NC | 0.4 (±2.6%) |
| CO | NC | 1.4 (±0.7%) |
| Z49 | 98.9 | 7.1 (±0.4%) |
| 95/5 | 98.5 | 35.0 (±0.1%) |
| Z56 | 93.7 | 18.9 (±0.3%) |
| Z13 | 91.6 | 27.9 (±0.3%) |
| Z10 | 97.4 | 36.2 (±0.2%) |
| 95/100 | 95.0 | 150.0 (±0.2%) |
| Z43 | 96.9 | 251.8 (±0.2%) |

DDA: Deacetylation degree; Mw: molecular weight; NC: Not calculable.

Turbidity Testing

The transmittance was measured via turbidity testing using the Varian Cary 50 Bio UV-Visible spectrometer (Agilent Technologies, USA) at 600 nm. Samples containing 2.7% hydroxyethyl cellulose were transferred to a cuvette and centrifuged at 600×g for 5 min in 50 ml plastic tubes to remove air pockets.

Semen Assessment

Semen samples of patients and volunteers collected at the Andrology, Sexual Medicine, Transmedicine, clinic (ANOVA, Karolinska University Hospital, Sweden) were run through standard semen kinematic analyses and sperm penetration assays no later than 3 h after collection. Data were obtained for the collection time, abstinence time, and semen volume. Semen was gently liquefied for 30 min on a rocker in an incubation chamber heated up to 37° C., after complete collection of ejaculates by masturbation. The viscosity of semen was determined visually and by pipetting. Semen was microscopically analysed by pipetting 6 μl of specimen in pre-warmed Leja® (Netherland) counting chamber slides (20 micron). Subsequently, specimens were assessed via clinical ECLIPSE 50i microscope (Nikon Instruments, Japan) equipped with stage heater MS 100 (37° C., Linkam Scientific Instruments, UK), 10× objective (Ph1)

and 0.5× charge coupled device camera UI-1540LE-M-HQ (IDS Imaging Development Systems GmbH, Germany) with total magnification of 5×. The system was connected to the Computer Aided Semen Analysis software QualiSperm (v3.0.9.486, AKYmed, Switzerland). Beside the sperm concentration [106/m1], the progressive motility [%], motility [%], immotility [%], velocity [μm/s], sperm size [μm2], and number of cells were measured. Semen samples meeting the following criteria were included in this study: volume of >1.5 ml, concentration of >15×106/mland >40% progressive motility. These criteria reflect reference limits of the World Health Organization (WHO) ("WHO Laboratory Manual for the Examination and Processing of Human Semen" 2010) and values for normal spermatozoa as stated in Bjorndahl (Lars Bjorndahl. 2011. "What Is Normal Semen Quality? On the Use and Abuse of Reference Limits for the Interpretation of Semen Analysis Results." Human Fertility 14 (3): 179-86). In each run, ten values were generated by assessing five fields in two chambers.

Cervical Mucus Assessment

Ovulatory cervical mucus (CVM) (the CVM with highest penetrability) was collected from healthy donors at the Karolinska University Hospital. Donors were not using hormonal contraceptives, were between 18 and 30 years old, had a BMI of 19-25, were non-smokers, and were neither under medication nor affected by chronic diseases. Before the collection of CVM, the hormonal status of each healthy, regularly cycling volunteer was examined by blood tests at the Karolinska University Laboratory. At the moment of donation, the woman's level of FSH, LH, and estradiol was analysed to prove the prevalence of ovulation. Mucus was collected at the external orifice using the endometrial catheters Gynebiops standard CH9 (GYNEAS, France) and Pipelle de Cornier for endometrial biopsy (PRODiMED, France).

In Vitro Fluorescence Profiling of Chitosan Diffusion into Cervical Mucus

To determine the diffusion distance and amount of chitosan accumulated in ovulatory CVM, a modified capillary diffusion assay in accordance to Wu, et al. (Seyoum Ayehunie, Ying-Ying Wang, Timothy Landry, Stephanie Bogojevic, and Richard A. Cone. 2018. "Hyperosmolal Vaginal Lubricants Markedly Reduce Epithelial Barrier Properties in a Three-Dimensional Vaginal Epithelium Model." Toxicology Reports 5 (January): 134-40) was performed. Labelled chitosan (Chitosan-FITC) of 0.5% (w/v) was adjusted to pH 5.5 (pH±0.02) by the use of 0.1/1 M hydrochloric acid (HCl, Merck KGaA, Germany), 0.1/1 M sodium hydroxide (NaOH, CPAchem Ltd., Bulgaria), or 50% NaOH (Sigma-Aldrich, USA).

CVM was aspirated into two capillaries by the use of customized square capillary tubes (L 60 mm, ID 0.3×0.3 mm, OD 0.45×0.45 mm, borosilicate glass) with Luer-connector (Hilgenberg GmbH, Germany) and 1 ml Soft-Ject® syringe (Henke-Sass Wolf GmbH, Germany). Next, the tubes were broken off at the Luer-connection, and the broken end sealed with wax (Paul Marienfeld GmbH & Co. KG, Germany). This resulted in an airtight capillary entirely filled with CVM. Septa of short thread caps (55° shore, Teknolab Sorbent AB, Sweden) were punctured with the sealed ends of capillaries, the caps placed on short threat glass vials (ND9, 1.5 ml, VWR, USA) and the open ends gently inserted into 300 μl of preheated buffer solution or Chitosan-FITC in buffer. CVM in capillaries treated with buffer solution served as negative control. Simultaneously, an identical square capillary without Luer-connector (L 50 mm, ID 0.3×0.3 mm, borosilicate glass, CM Scientific Ltd., UK) was filled with Chitosan-FITC solution by inserting the capillary into a glass vial containing 300 μl 0.5% or 0.1% Chitosan-FITC, functioning as positive control and reference fluorescence intensity. After 30 min incubation at 37° C. and 5% CO2, the capillaries were assessed via fluorescence microscopy and images in an exposure time range of 0.01 s-1 s recorded. Images were acquired via Eclipse Ti inverted microscope (Nikon, Japan), Zyla sCMOS camera (5.5 MP, Andor, Oxford Instruments, UK) and the light source pE-300lite (10 ms, CoolLED, UK) connected to the NIS-Elements BR 4.60.00 software (Nikon, Japan). Filter B for green fluorescence and a 2× objective were used. Images captured at an exposure time of 20 ms presented non-saturated images used to optimal identify differences in fluorescence intensity between different CS, and to calculate the chitosan quantity in CVM. At an exposure time of 800 ms, fluorescence signals were saturated at the beginning of the capillary, but low Chitosan-FITC concentrations were observed further inside the capillary, hence, acquiring the maximum diffusion distance.

Exported images were analysed by ImageJ software (version 2.0.0-rc-43/1.52b, USA). A rectangle was drawn in the middle of each capillary (h=15, w=1314), starting at 5 mm before the interface of air and CVM in the capillary, to also obtain the Chitosan-FITC accumulation at the interface. The fluorescence intensity was plotted over the distance in pixels. Each pixel corresponded to 3 μm. At an exposure time of 800 ms, with buffer-treated CVM showed a background signal, thus, the gained values were subtracted from the values obtained with Chitosan-FITC treated CVMs.

By the use of the control capillary with known Chitosan-FITC concentration, the fluorescence intensity along capillaries with unknown Chitosan-FITC concentration could be converted into Chitosan-FITC concentration. The relative amount of chitosan accumulated at 20 ms and the relative fluorescence intensity at 800 ms along the capillary was plotted using Prism 8 (GraphPad, USA). By calculating the area under the curve (AUC) for samples analysed at 0.02 s, the Chitosan-FITC accumulation was obtained.

Phase Contrast Microscopy of Spermatozoa Penetration

After the liquefaction and assessment of semen and CVM, 100 μl of buffer only and chitosan in buffer were filled in glass vials (ND9, 1.5 ml, VWR, USA) closed by caps with septum (55° shore, Teknolab Sorbent AB, Sweden), and pre-heated at 37° C. An aliquot of ovulatory CVM was aspirated into two customized capillaries and the capillaries were sealed at the broken end as described above. The septum of the cap was penetrated by the sealed end of the capillaries filled with CVM. The capillaries, embedded through the caps, were first placed in glass vials containing chitosan solutions for 30 min at 37° C. (5 mm deep into the solution). Then the capillaries were transferred to a glass vial containing 100 μl of semen for penetration of spermatozoa for 30 min at 37° C. (5 mm deep into the solution). For one control experiments, the same process was repeated but replacing chitosan solution with only buffer solution. For another control experiment, the same process was repeated but directly dipping the capillaries filled with ovulatory CVM in sperm. After incubation, the capillaries were placed on a customized microscopic glass slide marked with the distances 0.5, 1, 2, 3, 4, and 5 cm, positioned on a pre-warmed (37° C.) stage heater DC 95 (Linkam Scientific Instruments, UK), and observed by microscopy.

Videos were recorded at the distances marked on the glass slide, including the beginning of the capillary (0.1 cm), by the use of the Eclipse Ci phase contrast microscope (Nikon, Japan) equipped with UI-3240LE-C-HQ camera (IDS Imaging Development Systems, Germany). A magnification of 10× was used for the objective (Ph1) and camera, generating a total magnification of 100×. The recorded microscopic field was 0.21×0.27 mm, equivalent to 0.0567 mm2. A resolution of 1280×1024 pixel were used to record videos of three fields at each distance with 30 pictures per second. The recording started at the upper, outer surface of the capillary, followed by focusing through the capillary until reaching the lower surface, resulting in a 3-D scan through the capillary. Spermatozoa were counted in the volume (0.017 $mm^3$). The assay was conducted in triplicate using semen of different volunteers.

Results of Example 1

The impact of chitosan molar mass was evidenced by testing the diffusion of fluorescently labelled chitosans of various sizes through human ovulatory cervical mucus. Both chitosans of animal origin (extracted from the shells of crustaceans, CO, 95/5 and 95/100) and for the fungal based chitosans (Z49, Z56, Z13, Z10, Z43), the results (FIG. 1, FIG. 2) clearly show that smaller chitosan both penetrate in more depth and accumulate more into the mucus. It was very notable that the large chitosan (>100 kDa) was unable to penetrate within the mucus gel network, probably because of steric hindrances, and would thus not accumulate into the mucus. This will create a very superficial barrier, which could be very susceptible to disruption by shear stress for instance. Chitosans above 100 kDa were thus excluded for this reason.

The impact of the molar mass of chitosan on the barrier properties of human ovulatory cervical mucus was tested using formulation-containing chitosans of various molar masses. By using the sperm penetration assays, human sperm, and ovulatory cervical mucus, it could be identified that smaller chitosan that were effective in reinforcing porcine gastric mucin hydrogels and mucus expressed by colonic cell lines, could not stop the penetration of human sperm through the mucus. This was clearly evidenced for the CO chitosan in several different buffer systems (FIG. 3), in a pH of 5.5 and lactic acid buffer. Even when CO was formulated in combination with a larger chitosan (95/5) the formulation failed to provide barrier reinforcing effect.

Similarly, it was shown that fungal chitosans of 7.1 and 18.9 kDa were also not effective at stopping sperm penetration (FIG. 4), Z49 and Z56 respectively. On the contrary, it was found that by the use of fungal chitosans above 20 kDa (e.g. Z10), the average sperm penetration dramatically reduced compared to the control group (untreated mucus) and compared to mucus treated with the chitosan dissolution buffer only (FIG. 4).

The sized dependency for an effective barrier reinforcing effect is also shown for crustacean shell-derived chitosans (FIG. 5). The larger chitosan (150 kDa) could also stop sperm penetration in these assays. However, results from the chitosan diffusion (FIG. 1 and FIG. 2) clearly show the poor penetration in the mucus of the larger chitosan (150 kDa). Thus, the barrier formed by the larger chitosan (150 kDa) is due to a thin crosslinked layer at the interface of the mucus gel. In the well-controlled condition of the in vitro sperm penetration assay, such thin crosslinked layer can indeed lead to a barrier to sperm. However, such a thin layer is unlikely to sustain the shear and convective movements that are common in vivo. In contrasts, the more in-depth penetration of chitosans between 20 kDa and 100 kDa would constitute a sturdier barrier in vivo. We conclude that optimal chitosans to reinforce the barrier properties of human ovulatory cervical mucus are contained within the 20 kDa and 100 kDa range since these chitosans combine an in-depth penetration in the mucus with their ability to form effective barrier to sperm.

For the proper delivery of chitosan to the cervical canal, the chitosan formulation should contain excipients that increase the viscosity of the solution in order to increase the residency time of the formulation, and to avoid leakage. It is important that the excipients do not interact with the chitosan as to allow the full interaction with the mucus components. The selected gelling excipients should at least be known for their good biocompatibility, have no negative charges that could interact with positive changes of chitosan, and not have known interaction with chitosans. The compatibility of hydroxyethycellulose and chitosans was tested by measuring the transmittance of the mixtures. The absence of transmittance change suggests the absence of chitosan precipitates and good compatibility of chitosans with hydroxyethycellulose as a thickening agent (FIG. 6). The addition of fungal chitosans (Z10, 36.2 kDa) or animal-derived chitosans (CO, 1.4 kDa; 95/5, 35 kDa) at 0.5% (w/v) did not alter the tranmission, indicating the abscence of precipitate and the good solubility of the chitosans in these formulations. Glycerol and hydroxyethylcellulose were also combined with chitosan to test for possible alteration in the penetration of chitosan in human ovulatory cervical mucus. The results show that these excipients do not alter the penetration of the chitosan into the ovulatory cervical mucus (FIG. 7). The drop in fluorescence in FIG. 7 marks the maximum diffusion distance of chitosan only and chitosan blended with excipients after 30 minutes of exposure to the mucus. The barrier reinforcing effect on ovulatory cervical mucus was also unaltered by the presence of the excipients tested (FIG. 8).

Example 2

Figure 9A:
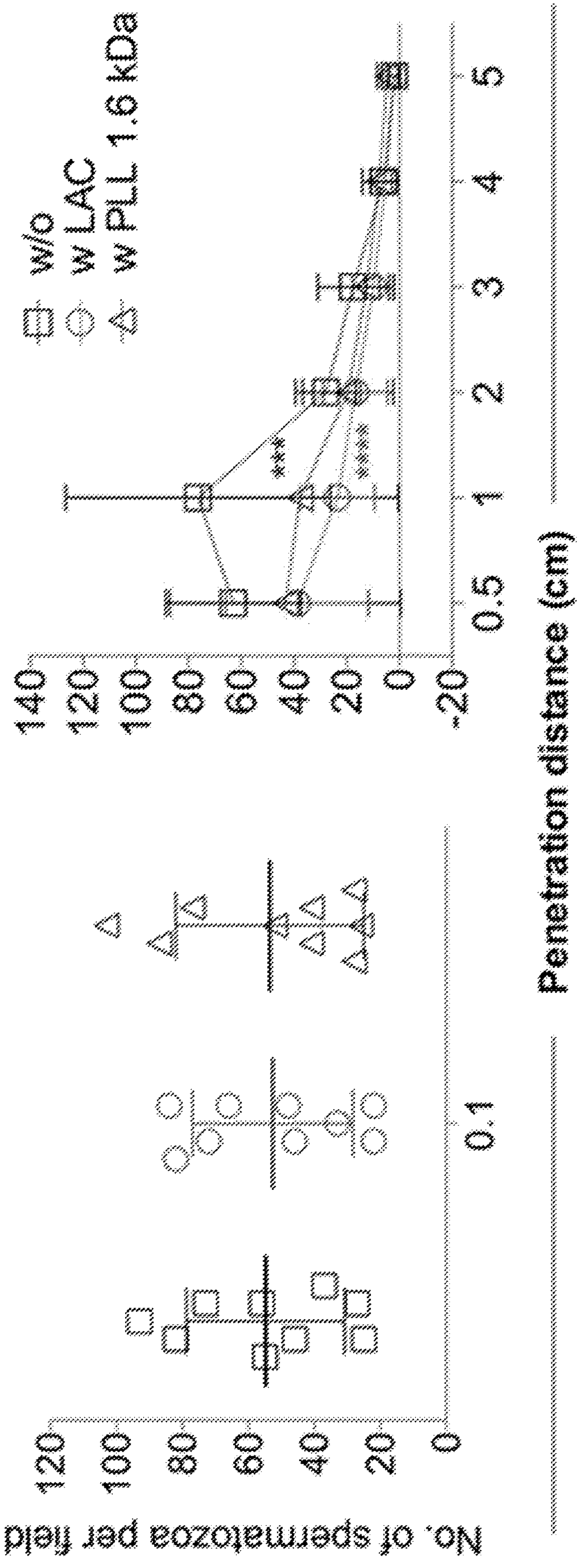
Figure 9B:
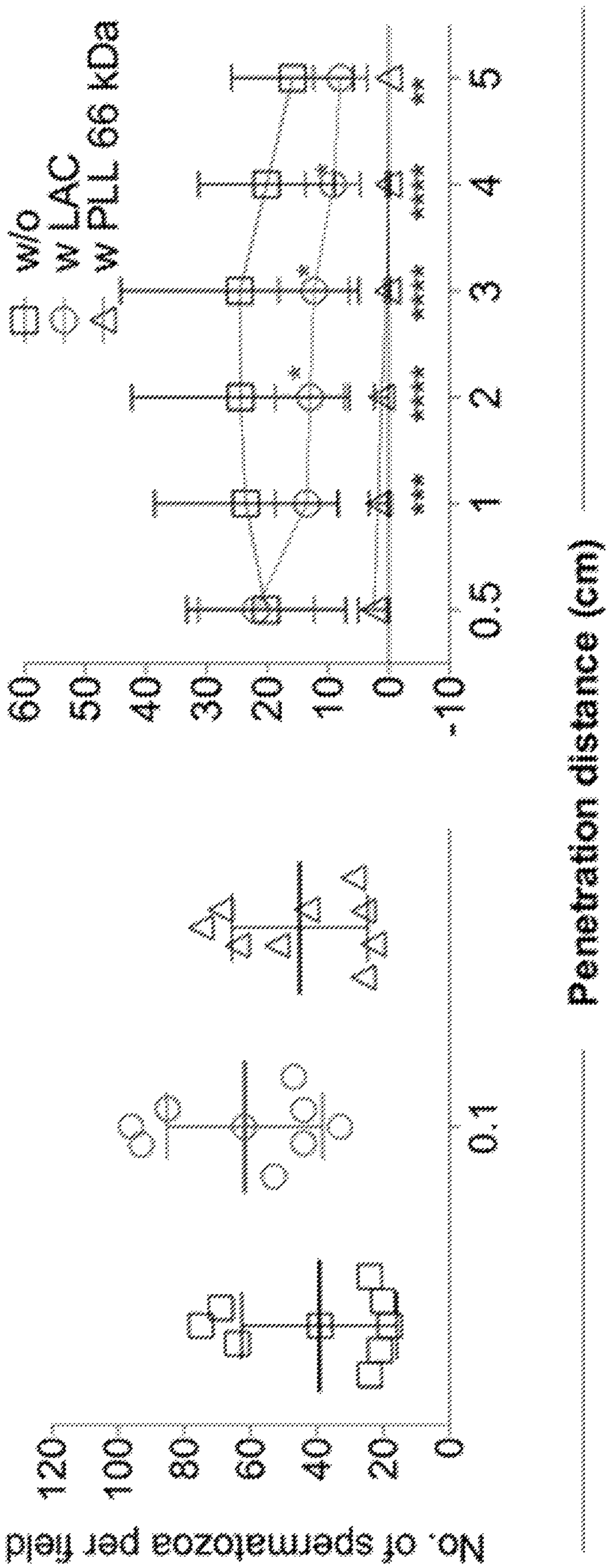

This example is to demonstrate mucus reinforcement by "amino acid monomers". In the present example is tested the penetration of human sperm into human ovulatory cervical mucus first exposed to a solution of poly-L-lysine (PLL). The results are presented in the FIGS. 9A and 9B showing sperm penetration assay performed on human ovulatory mucus. The sperm numbers were assessed 30 minutes after exposure to undiluted sperm.

Materials and methods used in example 2 are similar to the material and methods used in example 1 but performed by replacing chitosan with PLL.

FIG. 9A (left and right) shows human ovulatory cervical mucus exposed to low molar mass poly-L-lysine (wPLL, 1.6 kDa) in 32.5 mM lactic acid buffer, to lactic acid buffer (32.5 mM), or non-modified (w/o). FIG. 9B (left and right) shows human ovulatory cervical mucus exposed to high molar mass poly-L-lysine (wPLL, 66 kDa) in 32.5 mM lactic acid buffer, to lactic acid buffer (32.5 mM), or non-modified (w/o).

Results of Example 2

From the results, it can be deducted that the PLL compounds are able to reinforce the barrier properties of human ovulatory cervical mucus to sperm. Similarly to chitosan, the low molecular weight PLL did not have any effect. Only higher molecular weight was able to prevent the entrance of the sperm. The point at which no sperm is seen was further into the mucus (around 3 cm for the 66 KDa PLL) was similar to some chitosans such as the 7.1 kDa chitosan (around 2 cm, FIG. 4A), but further than with other chitosans such as the 27.9 kDa and 36.2 kDa (around 0.5 cm, FIGS. 4C and 4D).

The invention will hereafter be described by way of the following non-limiting items.

1. A vaginal contraceptive composition comprising one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.
2. The vaginal contraceptive composition according to any preceding item, wherein the vaginal contraceptive composition is not a foam.
3. The vaginal contraceptive composition according to any preceding item, wherein the mucoadhesive polymer has a molecular weight between 20.000 Da and 90.000 Da.
4. The vaginal contraceptive composition according to any preceding item, wherein the mucoadhesive polymer has a molecular weight between 20.000 Da and 75.000 Da.
5. The vaginal contraceptive composition according to any preceding item, wherein the mucoadhesive polymer has a molecular weight between 20.000 Da and 60.000 Da.
6. The vaginal contraceptive composition according to any preceding item, wherein the mucoadhesive polymer has a molecular weight between 30.000 Da and 50.000 Da.
7. The vaginal contraceptive composition according to any preceding item, wherein the mucoadhesive polymer has a molecular weight between 30.000 Da and 40.000 Da.
8. The vaginal contraceptive composition according to any preceding item, wherein said mucoadhesive polymer consists of a plurality of monomer units linked to each other via ether bonds.
9. The vaginal contraceptive composition according to any preceding item, wherein at least 55% of the monomer units comprise at least one amino group.
10. The vaginal contraceptive composition according to any preceding item, wherein at least 60% of the monomer units comprise at least one amino group.
11. The vaginal contraceptive composition according to any preceding item, wherein at least 65% of the monomer units comprise at least one amino group.
12. The vaginal contraceptive composition according to any preceding item, wherein at least 70% of the monomer units comprise at least one amino group.
13. The vaginal contraceptive composition according to any preceding item, wherein one or more of the at least one amino group are primary amines.
14. The vaginal contraceptive composition according to any preceding item, wherein the monomer units are selected from C6 sugars, amino-functionalised C6 sugars, or combinations hereof.
15. The vaginal contraceptive composition according to any preceding item, wherein the monomer units are amino-functionalised C6 sugars.
16. The vaginal contraceptive composition according to any preceding item, wherein the monomer units are a combination of D-glucosamine and N-acetyl-D-glucosamine.
17. The vaginal contraceptive composition according to item 16, wherein at least 50% is D-glucosamine.
18. The vaginal contraceptive composition according to any of items 16-17, wherein 50% or less is N-acetyl-D-glucosamine.
19. The vaginal contraceptive composition according to any of items 16-18, wherein between 50% and 100% is D-glucosamine.
20. The vaginal contraceptive composition according to any of items 16-19, wherein between 0% and 50% is N-acetyl-D-glucosamine.
21. The vaginal contraceptive composition according to any of items 16-20, wherein at least 65% is D-glucosamine.
22. The vaginal contraceptive composition according to any of items 16-21, wherein 35% or less is N-acetyl-D-glucosamine.
23. The vaginal contraceptive composition according to any of items 16-22, wherein between 65% and 100% is D-glucosamine.
24. The vaginal contraceptive composition according to any of items 16-23, wherein between 0% and 35% is N-acetyl-D-glucosamine.
25. The vaginal contraceptive composition according to any of items 1-7, wherein the mucoadhesive polymer is a peptide molecule of a length of 180 to 900 amino acids, which are linked via amide bonds.
26. The vaginal contraceptive composition according to item 25, wherein the mucoadhesive polymer is a polypeptide of amino acids, wherein at least 50% of the amino acids are 20 selected from the list consisting of arginine, lysine, histidine, ornithine, and β-alanine.
27. The vaginal contraceptive composition according to any of items 25-26, wherein the mucoadhesive polymer comprise poly-lysine, poly-orthinine, and/or poly-arginine.
28. The vaginal contraceptive composition according to item 27, wherein the mucoadhesive polymer comprise poly-lysine.
29. The vaginal contraceptive composition according to any of items 1-7, wherein the mucoadhesive polymer is a peptide molecule of a length of 180 to 900 amino acids 30 wherein at least 50% of the amino acids carry a hydrophobic group, which amino acids are selected from the list consisting of: alanine, methionine, cysteine, phenylalanine, leucine, valine, and isoleucine, and wherein the remaining amino acids may be selected from the list consisting of: glycine, serine, threonine, asparagine, and glutamine.
30. The vaginal contraceptive composition according to any of items 1-7, wherein the mucoadhesive polymer comprises amino acids, wherein at least 50% of the amino acids are selected from the group consisting of arginine, lysine, histidine, ornithine, and β-alanine, or 50% of the amino acids carries a hydrophobic group, and are selected from the group consisting of alanine, methionine, cysteine, phenylalanine, leucine, valine, and 40 isoleucine.
31. The vaginal contraceptive composition according to any of items 1-7, wherein the mucoadhesive polymer is a peptide molecule, which are linked via amide bonds, wherein at least 50% of the amino acids are selected from the list consisting of arginine, lysine, histidine, ornithine, and β-alanine.

32. The vaginal contraceptive composition according to item 31, wherein at least 60% of the amino acids are selected from the list consisting of arginine, lysine, histidine, ornithine, and β-alanine.

33. The vaginal contraceptive composition according to any of items 31-32, wherein at least 70% of the amino acids are selected from the list consisting of arginine, lysine, histidine, ornithine, and β-alanine.

34. The vaginal contraceptive composition according to any of items 1-7, wherein the mucoadhesive polymer is a peptide molecule, which are linked via amide bonds, wherein at least 50% of the amino acids are lysine.

35. The vaginal contraceptive composition according to item 34, wherein at least 60%, such as at least 70% of the amino acids are lysine.

36. The vaginal contraceptive composition according to any of items 1-7, wherein the mucoadhesive polymer comprises amino acids being L-lysine.

37. The vaginal contraceptive composition according to item 36, wherein the mucoadhesive polymer is poly-L-lysine (PLL).

38. The vaginal contraceptive composition according to any preceding item, wherein the physiological acceptable gelling agent is selected from hydroxyethyl cellulose (HEC), 30 glycerol, hydroxypropylmethyl cellulose (HPMC), hydroxypropyl cellulose, guar gum, or combinations hereof.

39. The vaginal contraceptive composition according to any preceding item, wherein said mucoadhesive polymer consists of 40 to 800 monomer units linked to each other via 35 ether bonds, ester bonds, amide bonds, or combinations hereof.

40. The vaginal contraceptive composition according to any preceding item, wherein said mucoadhesive polymer consists of 50 to 750 monomer units linked to each other via ether bonds, ester bonds, amide bonds, or combinations hereof.

41. The vaginal contraceptive composition according to any preceding item, wherein said mucoadhesive polymer consists of 75 to 700 monomer units linked to each other via ether bonds, ester bonds, amide bonds, or combinations hereof.

42. The vaginal contraceptive composition according to any preceding item, wherein said mucoadhesive polymer consists of 100 to 650 monomer units linked to each other via ether bonds, ester bonds, amide bonds, or combinations hereof.

43. The vaginal contraceptive composition according to any preceding item, wherein said mucoadhesive polymer consists of 150 to 600 monomer units linked to each other via ether bonds, ester bonds, amide bonds, or combinations hereof.

44. The vaginal contraceptive composition according to any preceding item, wherein the mucoadhesive polymer is in a concentration of between 0.05 wt. % and 10.0 wt. % of the total weight of the vaginal contraceptive composition.

45. The vaginal contraceptive composition according to any preceding item, wherein pH of the composition is between 2.0 and 7.0.

46. The vaginal contraceptive composition according to any preceding item, wherein pH of the composition is between 2.5 and 6.5.

47. The vaginal contraceptive composition according to any preceding item, wherein pH of the composition is between 3.0 and 6.0.

48. The vaginal contraceptive composition according to any preceding item, wherein the composition is a contraceptive composition.

49. Use of a vaginal contraceptive composition according to any of items 1-48 as a 30 contraceptive agent.

50. A vaginal contraceptive composition for use in therapy, wherein the vaginal contraceptive composition comprises one or more active ingredients and a physiological acceptable gelling agent, wherein at least one of the one or more active ingredients is a 35 mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and 40 wherein at least 50% of the monomer units comprise at least one amino group.

51. A vaginal contraceptive composition for use as a contraceptive or contraceptive agent, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

52. A vaginal contraceptive composition for use in birth control or birth control therapy, wherein the vaginal contraceptive composition comprises one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group.

53. The vaginal contraceptive composition according to item 50 or 51 or 52, wherein the vaginal contraceptive composition is not a foam.

54. The vaginal contraceptive composition according to any of items 50-53, wherein the mucoadhesive polymer has a molecular weight between 20.000 Da and 90.000 Da.

55. The vaginal contraceptive composition according to any of items 50-54, wherein the mucoadhesive polymer has a molecular weight between 30.000 Da and 75.000 Da.

56. The vaginal contraceptive composition according to any of items 50-55, wherein the mucoadhesive polymer has a molecular weight between 30.000 Da and 60.000 Da.
57. The vaginal contraceptive composition according to any of items 50-56, wherein the mucoadhesive polymer has a molecular weight between 30.000 Da and 50.000 Da.
58. The vaginal contraceptive composition according to any of items 50-57, wherein the 40 mucoadhesive polymer has a molecular weight between 30.000 Da and 40.000 Da.
59. The vaginal contraceptive composition according to any of items 50-58, wherein said mucoadhesive polymer consists of a plurality of monomer units linked to each other via ether bonds.
60. The vaginal contraceptive composition according to any of items 50-59, wherein at least 55% of the monomer units comprise at least one amino group.
61. The vaginal contraceptive composition according to any of items 50-60, wherein at least 60% of the monomer units comprise at least one amino group.
62. The vaginal contraceptive composition according to any of items 50-61, wherein at least 65% of the monomer units comprise at least one amino group.
63. The vaginal contraceptive composition according to any of items 50-62, wherein at least 70% of the monomer units comprise at least one amino group.
64. The vaginal contraceptive composition according to any of items 50-63, wherein the at least one amino group is a primary amine.
65. The vaginal contraceptive composition according to any of items 50-64, wherein the monomer units are selected from C6 sugars, amino-functionalised C6 sugars, or combinations hereof.
66. The vaginal contraceptive composition according to any of items 50-65, wherein the monomer units are amino-functionalised C6 sugars.
67. The vaginal contraceptive composition according to any of items 50-66, wherein the monomer units are a combination of D-glucosamine and N-acetyl-D-glucosamine.
68. The vaginal contraceptive composition according to item 67, wherein at least 50% is D-glucosamine.
69. The vaginal contraceptive composition according to any of items 67-68, wherein 50% or 35 less is N-acetyl-D-glucosamine.
70. The vaginal contraceptive composition according to any of items 67-69, wherein between 50% and 100% is D-glucosamine.
71. The vaginal contraceptive composition according to any of items 67-70, wherein between 0% and 50% is N-acetyl-D-glucosamine.
72. The vaginal contraceptive composition according to any of items 67-71, wherein at least 65% is D-glucosamine.
73. The vaginal contraceptive composition according to any of items 67-72, wherein 35% or less is N-acetyl-D-glucosamine.
74. The vaginal contraceptive composition according to any of items 67-73, wherein between 65% and 100% is D-glucosamine.
75. The vaginal contraceptive composition according to any of items 67-74, wherein between 0% and 35% is N-acetyl-D-glucosamine.
76. The vaginal contraceptive composition according to any of items 50-59, wherein the mucoadhesive polymer is a peptide molecule of a length of 180 to 900 amino acids, which are linked via amide bonds.
77. The vaginal contraceptive composition according to item 76, wherein the mucoadhesive polymer is a polypeptide of amino acids, wherein at least 50% of the amino acids are selected from the list consisting of arginine, lysine, histidine, ornithine, and β-alanine.
78. The vaginal contraceptive composition according to any of items 76-77, wherein the 25 mucoadhesive polymer comprise poly-lysine, poly-orthinine, and/or poly-arginine.
79. The vaginal contraceptive composition according to item 78, wherein the mucoadhesive polymer comprise poly-lysine.
80. The vaginal contraceptive composition according to any of items 50-59, wherein the mucoadhesive polymer is a peptide molecule of a length of 180 to 900 amino acids wherein at least 50% of the amino acids carry a hydrophobic group, which amino acids are selected from the list consisting of: alanine, methionine, cysteine, phenylalanine, leucine, valine, and isoleucine, and wherein the remaining amino acids may be selected 35 from the list consisting of: glycine, serine, threonine, asparagine, and glutamine.
81. The vaginal contraceptive composition according to any of items 50-59, wherein the mucoadhesive polymer comprises amino acids, wherein at least 50% of the amino acids are selected from the group consisting of arginine, lysine, histidine, ornithine, and 13-40 alanine, or 50% of the amino acids carries a hydrophobic group, and are selected from the group consisting of alanine, methionine, cysteine, phenylalanine, leucine, valine, and isoleucine.
82. The vaginal contraceptive composition according to any of items 50-15, wherein the mucoadhesive polymer is a peptide molecule, which are linked via amide bonds, wherein at least 50% of the amino acids are selected from the list consisting of arginine, lysine, histidine, ornithine, and β-alanine.
83. The vaginal contraceptive composition according to item 82, wherein at least 60% of the amino acids are selected from the list consisting of arginine, lysine, histidine, ornithine, and β-alanine.
84. The vaginal contraceptive composition according to any of items 82-83, wherein at least 70% of the amino acids are selected from the list consisting of arginine, lysine, histidine, ornithine, and β-alanine.
85. The vaginal contraceptive composition according to any of items 50-59, wherein the mucoadhesive polymer is a peptide molecule, which are linked via amide bonds, wherein at least 50% of the amino acids are lysine.
86. The vaginal contraceptive composition according to item 85, wherein at least 60%, such as at least 70% of the amino acids are lysine.
87. The vaginal contraceptive composition according to any of items 50-59, wherein the 25 mucoadhesive polymer comprises amino acids being L-lysine.
88. The vaginal contraceptive composition according to item 87, wherein the mucoadhesive polymer is poly-L-lysine (PLL).
89. The vaginal contraceptive composition according to any of items 50-88, wherein the physiological acceptable gelling agent is selected from hydroxyethyl cellulose (HEC), glycerol, hydroxypropylmethyl cellulose (HPMC), hydroxypropyl cellulose, guar gum, or combinations hereof.

90. The vaginal contraceptive composition according to any of items 50-89, wherein said mucoadhesive polymer consists of 40 to 800 monomer units linked to each other via ether bonds, ester bonds, amide bonds, or combinations hereof.

91. The vaginal contraceptive composition according to any of items 50-90, wherein said mucoadhesive polymer consists of 50 to 750 monomer units linked to each other via ether bonds, ester bonds, amide bonds, or combinations hereof.

92. The vaginal contraceptive composition according to any of items 50-91, wherein said mucoadhesive polymer consists of 75 to 700 monomer units linked to each other via ether bonds, ester bonds, amide bonds, or combinations hereof.

93. The vaginal contraceptive composition according to any of items 50-92, wherein said mucoadhesive polymer consists of 100 to 650 monomer units linked to each other via ether bonds, ester bonds, amide bonds, or combinations hereof.

94. The vaginal contraceptive composition according to any of items 50-93, wherein said mucoadhesive polymer consists of 150 to 600 monomer units linked to each other via ether bonds, ester bonds, amide bonds, or combinations hereof.

95. The vaginal contraceptive composition according to any of items 50-94, wherein the mucoadhesive polymer is in a concentration of between 0.05 wt. % and 10.0 wt. % of the total weight of the vaginal contraceptive composition.

96. The vaginal contraceptive composition according to any of items 50-95, wherein pH of the composition is between 2.0 and 7.0.

97. The vaginal contraceptive composition according to any of items 50-96, wherein pH of 25 the composition is between 2.5 and 6.5.

98. The vaginal contraceptive composition according to any of items 50-97, wherein pH of the composition is between 3.0 and 6.0.

The invention claimed is:

1. A vaginal contraceptive composition comprising one or more active ingredients and a physiological acceptable gelling agent, wherein at least one of the one or more active ingredients is a mucoadhesive polymer, wherein said mucoadhesive polymer has a molecular weight between 20.000 Da and 100.000 Da, wherein said mucoadhesive polymer consists of a plurality of monomer units linked to each other via ether bonds, ester bonds, amide bonds, or combinations hereof, wherein said monomer units are selected from C6 sugars, amino-functionalised C6 sugars, amino acids, or combinations hereof, and wherein at least 50% of the monomer units comprise at least one amino group, wherein the gelling agent does not have strong interactions with the mucoadhesive polymer and wherein the vaginal contraceptive composition is not a foam.

2. The vaginal contraceptive composition according to claim 1, wherein the mucoadhesive polymer has a molecular weight between 20.000 Da and 90.000 Da, such as between 30.000 Da and 75.000 Da, such as between 30.000 Da and 60.000 Da, such as between 30.000 Da and 50.000 Da, such as between 30.000 Da and 40.000 Da.

3. The vaginal contraceptive composition according to claim 1, wherein at least 55% of the monomer units comprise at least one amino group, such as at least 60% of the monomer units comprise at least one amino group, such as at least 65% of the monomer units comprise at least one amino group, such as at least 70% of the monomer units comprise at least one amino group.

4. The vaginal contraceptive composition according to claim 1, wherein the at least one amino group is a primary amine.

5. The vaginal contraceptive composition according to claim 1, wherein the monomer units are selected from C6 sugars, amino-functionalised C6 sugars, or combinations hereof.

6. The vaginal contraceptive composition according to claim 1, wherein the monomer units are amino-functionalised C6 sugars.

7. The vaginal contraceptive composition according to claim 1, wherein the monomer units are a combination of D-glucosamine and N-acetyl-D-glucosamine.

8. The vaginal contraceptive composition according to claim 7, wherein at least 50% is D-glucosamine and 50% or less is N-acetyl-D-glucosamine, such as between 50% and 100% is D-glucosamine and between 0% and 50% is N-acetyl-D-glucosamine, such as at least 65% is D-glucosamine and 35% or less is N-acetyl-D-glucosamine, such as between 65% and 100% is D-glucosamine and between 0% and 35% is N-acetyl-D-glucosamine.

9. The vaginal contraceptive composition according to claim 1, wherein the mucoadhesive polymer is a peptide molecule, which are linked via amide bonds.

10. The vaginal contraceptive composition according to claim 9, wherein the mucoadhesive polymer is a polypeptide of amino acids, wherein at least 50% of the amino acids are selected from the list consisting of arginine, lysine, histidine, ornithine, and β-alanine.

11. The vaginal contraceptive composition according to claim 9, wherein the mucoadhesive polymer comprise polylysine, poly-orthinine, and/or poly-arginine.

12. The vaginal contraceptive composition according to claim 1, wherein the physiological acceptable gelling agent is selected from hydroxyethyl cellulose (HEC), glycerol, hydroxypropylmethyl cellulose (HPMC), hydroxypropyl cellulose, guar gum, or combinations hereof.

13. The vaginal contraceptive composition according to claim 1, wherein the mucoadhesive polymer is in a concentration of between 0.05 wt. % and 10.0 wt. % of the total weight of the vaginal contraceptive composition.

14. The vaginal contraceptive composition according to claim 1, wherein pH of the composition is between 2.0 and 7.0, such as between 2.5 and 6.5, such as between 3.0 and 6.0.

15. The vaginal contraceptive composition according to claim 1, wherein the composition is a contraceptive composition.

16. A vaginal contraceptive composition for use as a contraceptive or contraceptive agent, wherein the vaginal contraceptive composition is a vaginal contraceptive composition according to claim 1.

17. A vaginal contraceptive composition for use in birth control or birth control therapy, wherein the vaginal contraceptive composition is a vaginal contraceptive composition according to claim 1.

18. The vaginal contraceptive composition according to claim 1, wherein the gelling agent is neutral or positively charged.

19. A method comprising using the vaginal contraceptive composition according to claim 1 as a contraceptive agent.

20. The method of claim 19, wherein the method comprises applying the composition to a vagina.

* * * * *